US012565524B2

(12) United States Patent
Xie et al.

(10) Patent No.: US 12,565,524 B2
(45) Date of Patent: Mar. 3, 2026

(54) METHODS FOR THE PRODUCTION OF CYTOPROTECTIVE ASIALO-ERYTHROPOIETIN IN PLANTS AND ITS PURIFICATION FROM PLANT TISSUES

(71) Applicant: NORTH CAROLINA CENTRAL UNIVERSITY, Durham, NC (US)

(72) Inventors: Jiahua Xie, Cary, NC (US); Farooqahmed S. Kittur, Durham, NC (US); Chiu-Yueh Hung, Raleigh, NC (US)

(73) Assignee: North Carolina Central University, Durham, NC (US)

( * ) Notice: Subject to any disclaimer, the term of this patent is extended or adjusted under 35 U.S.C. 154(b) by 0 days.

(21) Appl. No.: 14/403,231

(22) PCT Filed: Mar. 14, 2013

(86) PCT No.: PCT/US2013/031382
§ 371 (c)(1),
(2) Date: Nov. 24, 2014

(87) PCT Pub. No.: WO2013/180809
PCT Pub. Date: Dec. 5, 2013

(65) Prior Publication Data
US 2015/0119325 A1 Apr. 30, 2015

Related U.S. Application Data

(60) Provisional application No. 61/652,599, filed on May 29, 2012.

(51) Int. Cl.
| | |
|---|---|
| *C12N 5/04* | (2006.01) |
| *C07K 14/505* | (2006.01) |
| *C12N 5/14* | (2006.01) |
| *C12N 15/09* | (2006.01) |
| *C12N 15/63* | (2006.01) |
| *C12N 15/82* | (2006.01) |

(52) U.S. Cl.
CPC ........ *C07K 14/505* (2013.01); *C12N 15/8257* (2013.01); *C12N 5/04* (2013.01); *C12N 5/14* (2013.01); *C12N 15/82* (2013.01)

(58) Field of Classification Search
None
See application file for complete search history.

(56) References Cited

U.S. PATENT DOCUMENTS

| | | | | |
|---|---|---|---|---|
| 7,601,891 B2 * | 10/2009 | Bakker | .............. | C12N 15/8258 435/320.1 |
| 2006/0040353 A1 * | 2/2006 | Davidson | ............. | C12N 9/1051 435/69.1 |
| 2008/0003680 A1 * | 1/2008 | Bakker | ................ | C12N 9/1051 435/414 |
| 2009/0004302 A1 * | 1/2009 | Cyr | ....................... | A23L 1/3002 424/732 |
| 2009/0285830 A1 * | 11/2009 | Adams | ................. | C07K 16/242 424/158.1 |
| 2011/0105734 A1 * | 5/2011 | Kawasaki | ............ | C07K 14/505 530/397 |
| 2014/0112927 A1 * | 4/2014 | Chen | ...................... | C07K 16/10 530/387.3 |

FOREIGN PATENT DOCUMENTS

WO WO 02/53580 A2 7/2002

OTHER PUBLICATIONS

Bru et al. Plant protein purification using cloud point extraction (CPE). Abstract. Surfactant Science Series, Surfactants in Solution, vol. 64:367-377 (1996). (Year: 1996).*
Okada et al. Asialoerythropoietin has strong renoprotective effects against ischemia-reperfusion injury in a murine model. Transplantation vol. 84:504-510 (2007). (Year: 2007).*
Wang et al. Specificities of Ricinus communis agglutinin 120 interaction with sulfated galactose. FEBS Letters 585:3927-3934, (Nov. 2011). (Year: 2011).*
E2531 Sigma-Aldrich. Anti-Erythropoietin antibody produced in rabbit [online] [retrieved on Sep. 4, 2023]. Retrieved from: www.sigmaaldrich.com/US/en/product/sigma/e2531 (Year: 1996).*
Kittur, F., et al., "N-Glycosylation engineering of tobacco plants to produce asialoerythropoietin," *Plant Cell Reports*, Feb. 28, 2012, pp. 1233-1243, vol. 31(7), Springer-Verlag, Berlin, DE.

(Continued)

*Primary Examiner* — Joanne Hama
*Assistant Examiner* — Regina M DeBerry
(74) *Attorney, Agent, or Firm* — Alston & Bird LLP

(57) ABSTRACT

The present invention provides methods for the high-level production of recombinant human erythropoietin (rhuEPO) derivative, asialoerythropoietin (asialo-rhuEPO), in plants. The methods for producing asialo-rhuEPO comprise making a plant or at least one plant cell that comprises a promoter that drives expression in a plant cell operably linked to a polynucleotide encoding a human erythropoieting fusion protein and a promoter that drives expression in a plant cell operably linked to a polynucleotide encoding N-glycosylation modification enzyme, particularly a mammalian β1, 4-galactosyltransferase. The present invention further provides plants, plant cells, and seeds that have been genetically modified to produce high levels of asialo-rhuEPO. Additionally, provided are methods for purifying asialo-rhuEPO from plant tissues. Such methods comprise removing chlorophyll and/or RuBisCO protein from an aqueous extract of plant tissue comprising asialo-rhuEPO, binding the asialo-rhuEPO in the extract to an immune affinity column, and eluting the bound asialo-rhuEPO from immune affinity column.

12 Claims, 14 Drawing Sheets
Specification includes a Sequence Listing.

(56)                    References Cited

OTHER PUBLICATIONS

Musa, T., et al., "Overexpression of human erythropoietin in tobacco does not affect plant fertility or morphology," *Plant Biotechnology Reports*, Mar. 22, 2009, pp. 157-165, vol. 3(2), Korean Society for Plant Biotechnology and Springer 2009.

Parsons, J., et al., "Moss-based production of asialo-erythropoietin devoid of Lewis A and other plant-typical carbohydrate determinants," *Plant Biotechnology Journal*, Sep. 24, 2012, pp. 851-861, vol. 10(7), Society for Experimental Biology, Association of Applied Biologists and Blackwell Publishing Ltd.

Yamasaki, N., and K. Ikebe, "A New Amylose Derivative for the Preparation of Protein-Carbohydrate Conjugates," *Bioscience Biotechnology Biochemistry*, Jan. 1, 1992, pp. 2091-2092, vol. 56(12), Japan Society for Bioscience, Biotechnology, and Agrochemistry, Tokyo, Japan.

Arthur et al., "Plant-Produced Asialo-Erythropoietin Restores Pancreatic Beta-Cell Function by Suppressing Mammalian Sterile-20-like Kinase (MST1) and Caspase-3 Activation," Frontiers in Pharmacology, 8(208), 10 pages, (2017).

Bakker, H., et al., "Galactose-extended glycans of antibodies produced by transgenic plants," Proc Natl Acad Sci USA, 98(5):2899-904, (2001).

Bakker, H., et al., "An antibody produced in tobacco expressing a hybrid beta-1,4-galactosyltransferase is essentially devoid of plant carbohydrate epitopes," Proc Nat Acad Sci USA, 103(20):7577-82, (2006).

Castilho, A., et al., "N-glycosylation engineering of plants for the biosynthesis of glycoproteins with bisected and branched complex N-glycans," Glycobiology, 21(6):813-823, (2011).

Cheon, B.Y., et al., "Overexpression of human erythropoietin (EPO) affects plant morphologies: retarded vegetative growth in tobacco and male sterility in tobacco and *Arabidopsis*," Transgenic Res., 13(6):541-549, (2004).

Conley, A.J., et al., "Plant recombinant erythropoietin attenuates inflammatory kidney cell injury," Plant Biotechnology Journal, 7:183-199, (2009).

Denecke, J., et al., "Protein Secretion in Plant Cells Can Occur via a Default Pathway," The Plant Cell, 2:51-59, (1990).

Gomord, V., et al., "Posttranslational modification of therapeutic proteins in plants," Curr Opin Plant Biol., 7(2):171-181, (2004).

Hamilton et al., "Humanization of Yeast to Produce Complex Terminally Sialylated Glycoproteins," Science, 313(5792):1441-1443, (2006).

Kittur et al., "Recombinant asialoerythropoetin protects HL-1 cardiomyocytes from injury via suppression of Mst1 activation," Biochemistry and Biophysics Reports, 17:157-168, (2019).

Kittur et al., "Cytoprotective Effect of Recombinant Human Erythropoietin Produced in Transgenic Tobacco Plants," PLoS One 8(10):e76468, 10 pages, (2013).

Lerouge, P., et al., "N-glycoprotein biosynthesis in plants: recent developments and future trends," Plant Mol Biol., 38:31-48, (1998).

Li et al., "Optimization of humanized IgGs in glycoengineered ichia pastoris," Nat Biotechnol., 24(2):210-215, (2006).

International Search Report and Written Opinion for International Application No. PCT/US2013/031382, mailed Jun. 21, 2013.

Ma J.K., et al., "The production of recombinant pharmaceutical proteins in plants," Nat Rev Genet., 4:794-805, (2003).

Misaki, R., et al., "Plant cultured cells expressing human β1,4-galactosyltransferase secrete glycoproteins with galactose-extended N-linked glycans," Glycobiology, 13:199-205, (2003).

Palacpac, N.Q., et al., "Stable expression of human beta1,4-galactosyltransferase in plant cells modifies N-linked glycosylation patterns," Proc Natl Acad Sci USA, 96(8):4692-4697, (1999).

Robic, G., et al., "Application of electrochemically produced aluminum hydroxide gel for prepurification of recombinant synthetic green fluorescent protein produced in tobacco leaves," Biotechnol Prog., 27:1029-1035, (2011).

Wasley, L.C., et al., "The Importance of N- and O-Linked Oligosaccharides for the Biosynthesis and In Vitro and In Vivo Biologic Activities of Erythropoietin," Blood, 77:2624-32 (1991).

Wee, E., et al., "Targeting of active sialytransferase to the plant golgi apparatus," The Plant Cell, 10:1759-1768, (1998).

Weise, A., et al., "High-level expression of secreted complex glycosylated recombinant human erythropoietin in the Physcomitrella Δ-fuc-tΔ-xyl-t mutant," Plant Biotechnology Journal, 5:389-401, (2007).

Zeng, Y., et al., "Purification and specificity of β1,4-xylosytransferase, an enzyme that contributes to the allergenicity of some plant proteins," J Biol Chem., 272:31340-31347, (1997).

* cited by examiner

APPRLICDSRVLQRYLLEAKEAENITTGCAEHCSLNE
NITVPDTKVNFYAWKRMEVGQQAVEVWQGLALLS
EAVLRGQALLVNSSQPWEPLQLHVDKAVSGLRSLTT
LLRALGAQKEAISPPDAASAAPLRTITADTFRKLFRVY
SNFLRGKLKLYTGEACRTGDR

FIG. 8

APPRLICDSRVLQRYLLEAKEAENITTGCAEHCSLNE
NITVPDTKVNFYAWKRMEVGQQAVEVWQGLALLS
EAVLRGQALLVNSSQPWEPLQLHVDKAVSGLRSLTT
LLRALGAQKEAISPPDAASAAPLRTITADTFRKLFRVY
SNFLRGKLKLYTGEACRTGDR

FIG. 10

SEQUENCE LISTING

```
<160> NUMBER OF SEQ ID NOS: 19

<210> SEQ ID NO 1
<211> LENGTH: 636
<212> TYPE: DNA
<213> ORGANISM: Artificial Sequence
<220> FEATURE:
<223> OTHER INFORMATION: Artificial Sequence of human EPO fusion protein
<220> FEATURE:
<221> NAME/KEY: misc_feature
<222> LOCATION: (1)...(579)
<223> OTHER INFORMATION: humam EPO domain coding region
<220> FEATURE:
<221> NAME/KEY: misc_feature
<222> LOCATION: (580)...(600)
<223> OTHER INFORMATION: TEV protease cleavage domain coding region
<220> FEATURE:
<221> NAME/KEY: misc_feature
<222> LOCATION: (601)...(624)
<223> OTHER INFORMATION: StrepII tag domain coding region
<220> FEATURE:
<221> NAME/KEY: misc_feature
<222> LOCATION: (625)...(636)
<223> OTHER INFORMATION: KDEL domain coding region

<400> SEQUENCE: 1
atgggggtgc acgaatgtcc tgcctggctg tggcttctcc tgtccctgct gtcgctccct        60
ctgggcctcc cagtcctggg cgccccacca cgcctcatct gtgacagccg agtcctggag       120
aggtacctct tggaggccaa ggaggccgag aatatcacga cgggctgtgc tgaacactgc       180
agcttgaatg agaatatcac tgtcccagac accaaagtta atttctatgc ctggaagagg       240
atggaggtcg ggcagcaggc cgtagaagtc tggcagggcc tggccctgct gtcggaagct       300
gtcctgcggg gccaggccct gttggtcaac tcttcccagc cgtgggagcc cctgcagctg       360
catgtggata aagccgtcag tggccttcgc agcctcacca ctctgcttcg ggctctggga       420
gcccagaagg aagccatctc ccctccagat gcggcctcag ctgctccact ccgaacaatc       480
actgctgaca ctttccgcaa actcttccga gtctactcca atttcctccg gggaaagctg       540
aagctgtaca caggggaggc ctgcaggaca ggggacagag aaaacctgta ttttcagggc       600
tggagtcatc ctcaatttga aagaaagat gaactc                                  636

<210> SEQ ID NO 2
<211> LENGTH: 212
<212> TYPE: PRT
<213> ORGANISM: Artificial Sequence
<220> FEATURE:
<223> OTHER INFORMATION: Artificial Sequence of human EPO fusion protein
<220> FEATURE:
<221> NAME/KEY: DOMAIN
<222> LOCATION: (1)...(193)
<223> OTHER INFORMATION: human EPO domain
<220> FEATURE:
<221> NAME/KEY: DOMAIN
<222> LOCATION: (194)...(200)
<223> OTHER INFORMATION: TEV protease cleavage domain
<220> FEATURE:
<221> NAME/KEY: DOMAIN
<222> LOCATION: (201)...(208)
<223> OTHER INFORMATION: StrepII tag domain
<220> FEATURE:
<221> NAME/KEY: DOMAIN
<222> LOCATION: (209)...(212)
```

-continued

```
<223> OTHER INFORMATION: KDEL endoplasmic reticulum retention signal
      domain

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg Glu Asn Leu Tyr Phe Gln Gly Trp Ser His Pro Gln Phe Glu Lys
            195                 200                 205

Lys Asp Glu Leu
    210

<210> SEQ ID NO 3
<211> LENGTH: 579
<212> TYPE: DNA
<213> ORGANISM: Homo sapiens
<220> FEATURE:
<221> NAME/KEY: misc_feature
<222> LOCATION: (1)...(579)
<223> OTHER INFORMATION: Coding region of human EPO of Accession No.
      NM_000799

<400> SEQUENCE: 3 atggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggaggtcg ggcagcaggc cgtagaagtc tggcagggcc tggccctgct gtcggaagct     300
gtcctgcggg gccaggccct gttggtcaac tcttcccagc cgtgggagcc cctgcagctg     360
catgtggata aagccgtcag tggccttcgc agcctcacca ctctgcttcg ggctctggga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca caggggaggc ctgcaggaca ggggacaga                            579
```

-continued

```
<210> SEQ ID NO 4
<211> LENGTH: 193
<212> TYPE: PRT
<213> ORGANISM: Homo sapiens
<220> FEATURE:
<221> NAME/KEY: DOMAIN
<222> LOCATION: (1)...(193)
<223> OTHER INFORMATION: human EPO protein of Accession No. NP_000790

<400> SEQUENCE: 4

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 5
<211> LENGTH: 7
<212> TYPE: PRT
<213> ORGANISM: Artificial Sequence
<220> FEATURE:
<223> OTHER INFORMATION: TEV protease cleavage domain

<400> SEQUENCE: 5

Glu Asn Leu Tyr Phe Gln Gly
1               5

<210> SEQ ID NO 6
<211> LENGTH: 8
<212> TYPE: PRT
<213> ORGANISM: Artificial Sequence
<220> FEATURE:
<223> OTHER INFORMATION: StepII tag domain

<400> SEQUENCE: 6

Trp Ser His Pro Gln Phe Glu Lys
1               5

<210> SEQ ID NO 7
```

-continued

```
<211> LENGTH: 4
<212> TYPE: PRT
<213> ORGANISM: Artificial Sequence
<220> FEATURE:
<223> OTHER INFORMATION: KDEL endoplasmic reticulum retention signal
      domain

<400> SEQUENCE: 7

Lys Asp Glu Leu
1

<210> SEQ ID NO 8
<211> LENGTH: 4
<212> TYPE: PRT
<213> ORGANISM: Artificial Sequence
<220> FEATURE:
<223> OTHER INFORMATION: HDEL endoplasmic reticulum retention signal
      domain

<400> SEQUENCE: 8

His Asp Glu Leu
1

<210> SEQ ID NO 9
<211> LENGTH: 784
<212> TYPE: DNA
<213> ORGANISM: Artificial Sequence
<220> FEATURE:
<223> OTHER INFORMATION: Double CaMV 35S promoter

<400> SEQUENCE: 9
gaaaatcttc gtcaacatgg tggagcacga cacgcttgtc tacctccaaa aatatcaaag       60
atacagtctc agaagaccaa agggaattga gactttcaa caaagggtaa tatccggaaa      120
cctcctcgga ttccattgcc cagctatctg tcactttatt gtgaagatag tggaaaagga      180
aggtggctcc tacaaatgcc atcattgcga taaaggaaag gccatcgttg aagatgcctc      240
tgccgacagt ggtcccaaag atggacccc acccacgagg agcatcgtgg aaaaagaaga      300
cgttccaacc acgtcttcaa agcaagtgga ttgatgtgat aacatggtgg agcacgacac      360
gcttgtctac ctccaaaaat atcaaagata cagtctcaga agaccaaagg gaattgagac      420
ttttcaacaa agggtaatat ccggaaacct cctcggattc cattgcccag ctatctgtca      480
ctttattgtg aagatagtgg aaaaggaagg tggctcctac aaatgccatc attgcgataa      540
aggaaaggcc atcgttgaag atgcctctgc cgacagtggt cccaaagatg gaccccacc      600 cacgaggagc atcgtggaaa aagaagacgt tccaaccacg tcttcaaagc aagtggattg      660
atgtgatatc tccactgacg taagggatga cgcacaatcc cactatcctt cgcaagaccc      720
ttcctctata taaggaagtt catttcattt ggagaggaca cgctgaaatc accagtctct      780
ctct                                                                   784

<210> SEQ ID NO 10
<211> LENGTH: 1194
<212> TYPE: DNA
<213> ORGANISM: Homo sapiens
<220> FEATURE:
<221> NAME/KEY: misc_feature
<222> LOCATION: (1)...(1194)
<223> OTHER INFORMATION: Human beta 1,4- galactosyltransferase 1 DNA
      sequence of beta 1,4- galactosyltransferase 1:
      coding region of Acession No. NM_001497

<400> SEQUENCE: 10
atgaggcttc gggagccgct cctgagcggc agcgccgcga tgccaggcgc gtccctacag       60
```

```
cgggcctgcc gcctgctcgt ggccgtctgc gctctgcacc ttggcgtcac cctcgtttac      120
tacctggctg gccgcgacct gagccgcctg ccccaactgg tcggagtctc cacaccgctg      180
cagggcggct cgaacagtgc cgccgccatc gggcagtcct ccggggagct ccggaccgga      240
ggggcccggc cgccgcctcc tctaggcgcc tcctcccagc cgcgcccggg tggcgactcc      300
agcccagtcg tggattctgg ccctggcccc gctagcaact tgacctcggt cccagtgccc      360
cacaccaccg cactgtcgct gcccgcctgc cctgaggagt ccccgctgct tgtgggcccc      420
atgctgattg agtttaacat gcctgtggac ctggagctcg tggcaaagca gaacccaaat      480
gtgaagatgg gcggccgcta tgcccccagg gactgcgtct ctcctcacaa ggtggccatc      540
atcattccat tccgcaaccg gcaggagcac ctcaagtact ggctatatta tttgcaccca      600
gtcctgcagc gccagcagct ggactatggc atctatgtta tcaaccaggc gggagacact      660
atattcaatc gtgctaagct cctcaatgtt ggctttcaag aagccttgaa ggactatgac      720
tacacctgct ttgtgtttag tgacgtggac ctcattccaa tgaatgacca taatgcgtac      780
aggtgttttt cacagccacg gcacatttcc gttgcaatgg ataagtttgg attcagccta      840
ccttatgttc agtattttgg aggtgtctct gctctaagta aacaacagtt tctaaccatc      900
aatggatttc ctaataatta ttggggctgg ggaggagaag atgatgacat ttttaacaga      960
ttagttttta gaggcatgtc tatatctcgc ccaaatgctg tggtcgggag gtgtcgcatg     1020
atccgccact caagagacaa gaaaaatgaa cccaatcctc agaggtttga ccgaattgca     1080
cacacaaagg agacaatgct ctctgatggt ttgaactcac tcacctacca ggtgctggat     1140
gtacagagat acccattgta tacccaaatc acagtggaca tcgggacacc gagc           1194
```

```
<210> SEQ ID NO 11
<211> LENGTH: 398
<212> TYPE: PRT
<213> ORGANISM: Homo sapiens
<220> FEATURE:
<221> NAME/KEY: DOMAIN
<222> LOCATION: (1)...(398)
<223> OTHER INFORMATION: beta 1,4- galactosyltransferase 1 of Accession
      No. NP_001488

<400> SEQUENCE: 11

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
65                  70                  75                  80

Gly Ala Arg Pro Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140
```

-continued

```
Phe Asn Met Pro Val Asp Leu Glu Leu Val Ala Lys Gln Asn Pro Asn
145             150                 155                 160

Val Lys Met Gly Gly Arg Tyr Ala Pro Arg Asp Cys Val Ser Pro His
            165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
            195                 200                 205

Tyr Gly Ile Tyr Val Ile Asn Gln Ala Gly Asp Thr Ile Phe Asn Arg
            210                 215                 220

Ala Lys Leu Leu Asn Val Gly Phe Gln Glu Ala Leu Lys Asp Tyr Asp
225             230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
                260                 265                 270

Met Asp Lys Phe Gly Phe Ser Leu Pro Tyr Val Gln Tyr Phe Gly Gly
            275                 280                 285

Val Ser Ala Leu Ser Lys Gln Gln Phe Leu Thr Ile Asn Gly Phe Pro
    290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
            355                 360                 365

Asp Gly Leu Asn Ser Leu Thr Tyr Gln Val Leu Asp Val Gln Arg Tyr
    370                 375                 380

Pro Leu Tyr Thr Gln Ile Thr Val Asp Ile Gly Thr Pro Ser
385                 390                 395
```

```
<210> SEQ ID NO 12
<211> LENGTH: 1291
<212> TYPE: DNA
<213> ORGANISM: Nicotiana tabacum
<220> FEATURE:
<221> NAME/KEY: promoter
<222> LOCATION: (1)...(1291)
<223> OTHER INFORMATION: Tobacco glyceraldehyde-3-phosphate
      dehydrogenase gene (GapC) promoter

<400> SEQUENCE: 12
tctagaatgt tcgtgcgtca aatggataaa caaaaaaata gcataagtta gttttgttac      60
tcgagagtta tgtattataa ggtataggga aatgactcaa acataccact gaacttaacg     120
aaacgacgca tatatatact acttaactta acgaaaaagg ggtgagagtg gatgggtgct     180
ggtaaataat gaagggttta tataacgtca cgtgtcaaaa ttcgatagta gtagtttcgt     240
tagttgtaat agcatatatg gcccaaagtt ataatataga taatatgttt atgtccaact     300
attaacgagt gacatagaca gttcattttg tgaagttcaa tgacatattt gagcccttc     360 cctttttatta tctccttttta tttgttctaa taaagaatg gcatttatta tgtacataga     420
caaataacta ttttctttgg aatataattt gtttatatat tttaaaatca tgtctcaatt     480
tagtttgttt tgtgcatatt tcaactattc aattttgtcc atatatttat taccttcccc     540
```

-continued

```
catttacaag cattgaaccg ctttgctcac caaaacttat gcacattgca aaaatatcat      600
gtaaaggttt tatgtatgct gtaattaagg tctgaactca tcgtgatttt atttttaggc      660
ttcattgacc actaccaaac tctttgatgc tacattttct aattatattg gagttcgatt      720
atatccgaat tcgcgttgcg tagggcccat tcgagggaaa acactcccta tcaaggattt      780
tttcataccc agagctcgaa ctcaagacat ctggttaagg gaagaacagt ctcatccact      840
gcaccatatc cttttgtggt caacaagtaa attttatgta gaaccaaaaa ctatactcga      900
attgataaaa taaatggtgt aaaatattgt tttctttctt acattttgga cagtaaatat      960
gtaggacaat aataattagc gtggggtctt aagaaaatta gcatagattt ccagaaattc     1020
caaatcaacc ggcagttcca ggtttgaaaa ctacaactca ttccgacggt tcaaacttca     1080
aaccatgctt gctgactcgg cttcttcttt ctttttcacc aagacagagc agtagtcacg     1140
tgacacccct cacgtgcctc cccccttat atttcagact gcaaccctac actttcgcta     1200
cattcactac catattcttt tcactaagca attttctctc ctactttct ttaaaccccct     1260 tttttctccc ctaagccatg gcatctagat c                                   1291
```

```
<210> SEQ ID NO 13
<211> LENGTH: 497
<212> TYPE: DNA
<213> ORGANISM: Nicotiana tabacum
<220> FEATURE:
<221> NAME/KEY: terminator
<222> LOCATION: (1)...(497)
<223> OTHER INFORMATION: Tobacco GapC terminator

<400> SEQUENCE: 13
gagctcgtga aatggcctct ttagtttttg attgaatcat aggggtatta gttttctatg       60
gccgggagtg gtcttcttgc ttaattgtaa tggaataacc agagaggaac tactgtgtta      120
tctttgagga atgttgggct tttttcgttt gaattatcat gaatgaaatt ttacttttc      180 ccaatacaag tttgttttcg tttcttggtt tttgttatcc cttggtttat gtcttggttt      240
ggcttaaatg attgaagatt acactaccta tgtttctgct attcctgttg aagatcacat      300
ttgataataa tgcatcgaat gcattaaagt ttcttattgg ctctgtcaaa agtattgaag      360
gtggattttt ctaattggca agagaaagta ttaaagaggt gatttattag tacttatatt      420
tttctcagca tctctctttc agtgttggag cttcataaaa ttagcacttc agagtttcag      480
tcgggagctg aattcga                                                     497
```

```
<210> SEQ ID NO 14
<211> LENGTH: 42
<212> TYPE: DNA
<213> ORGANISM: homo sapiens

<400> SEQUENCE: 14
taattctaga atgcaccatc atcatcatca tggggtgcac ga                          42
```

```
<210> SEQ ID NO 15
<211> LENGTH: 42
<212> TYPE: DNA
<213> ORGANISM: homo sapiens

<400> SEQUENCE: 15
aattgagctc ctagagctca tcttttctgt cccctgtcct gc                          42
```

```
<210> SEQ ID NO 16
<211> LENGTH: 21
```

-continued

```
<212> TYPE: DNA
<213> ORGANISM: homo sapiens

<400> SEQUENCE: 16
ctggctatat tatttgcacc c                                          21

<210> SEQ ID NO 17
<211> LENGTH: 20
<212> TYPE: DNA
<213> ORGANISM: homo sapiens

<400> SEQUENCE: 17
attgtctcct ttgtgtgtgc                                            20

<210> SEQ ID NO 18
<211> LENGTH: 22
<212> TYPE: DNA
<213> ORGANISM: homo sapiens

<400> SEQUENCE: 18
aagatggatt gcacgcaggt tc                                         22

<210> SEQ ID NO 19
<211> LENGTH: 21
<212> TYPE: DNA
<213> ORGANISM: homo sapiens

<400> SEQUENCE: 19
acgggtagcc aacgctatgt c                                          21
```

METHODS FOR THE PRODUCTION OF CYTOPROTECTIVE ASIALO-ERYTHROPOIETIN IN PLANTS AND ITS PURIFICATION FROM PLANT TISSUES

CROSS-REFERENCE TO RELATED APPLICATIONS

This application is the U.S. National Stage of International Patent Application No. PCT/US2013/031382, filed Mar. 14, 2013, which designates the U.S. and was published by the International Bureau in English on Aug. 20, 2009, and which claims the benefit of U.S. Provisional Patent Application No. 61/652,599, filed May 29, 2012; all of which are hereby incorporated herein in their entirety by reference.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 20160808 453783 SSL.txt, created on Aug. 8, 2016, and having a size of 17 kilobytes, and is filed concurrently with the specification. The sequence listing contained in this ASCII formatted document is part of the specification and is herein incorporated by reference in its entirety.

BACKGROUND OF THE INVENTION

Erythropoietin (EPO) is a glycoprotein hormone (Krantz and Jacobson 1970), which consists of a single polypeptide chain of 165 amino acids containing three N-linked and one O-linked glycan chains (Sasaki et al. 1987; Takeuchi & Kobata 1991; Jelkmann 1992). Currently, recombinant human EPO (rhuEPO) is widely used to treat anemia associated with chronic renal failure, AIDS, rheumatoid arthritis, malignancies and many other types of anemia (Jelkmann 1992, 2005; Smith et al. 2003). It is the most commercially valuable biopharmaceutical on the market with US $12 billion annual market value (Tucker and Yakatan 2008). EPO is a sialoglycoprotein that requires proper N-glycosylation for its stability and in vivo biological activity (Wasley et al. 1991). Terminal sialic acid residues are indispensable for its in vivo biological activity, mainly by preventing its clearance by galactose binding receptors on hepatocytes (Morell et al. 1971; Fukuda et al. 1989; Toledo et al. 2006). The penultimate β1,4-linked galactose residues are also important for in vivo activity, since removal of these residues has been shown to cause dramatic reduction in in vivo biological activity (Wasley et al. 1991).

The primary function of EPO is to regulate erythrocyte production (Jelkmann 1992, 2005; Sherwood 1984). In addition to this, using animal models, EPO has been found to protect brain, heart, and kidneys against diverse injuries (Gong et al. 2004; Calvillo et al. 2003; Moon et al. 2003; Parsa et al. 2004). These two functions are mediated by binding of EPO to two distinct receptors: hematopoiesis via activation of homodimeric receptor complex $(EPOR)_2$ in erythroid cells (Fisher 2003) and tissue protection through activation of heterodimeric receptor composed of EPOR and CD131 (β common receptor, βcR), which is expressed in brain, heart and kidney (Brines et al. 2004). Recent studies have shown that the two activities are dissociable either by chemical modification or genetically altering the EPO molecule (Leist et al. 2004; Brines et al. 2008). Another distinguishable feature between hematopoietic and tissue protective functions is that erythrocyte production requires constant presence of EPO, whereas a brief exposure to high doses is enough for neuroprotection both in vitro and in vivo (Morishita et al. 1997; Erbayraktar et al. 2003).

Although rhuEPO displays tissue protective function, it cannot be used directly for cytoprotective purposes because of its undesirable side effects leading to harmful increases in the red blood cell mass (Erbayraktar et al. 2003; Wiessner et al. 2001). Recent studies have shown that rhuEPO derivatives, such as asialo-rhuEPO generated by total enzymatic desialylation of rhuEPO, and CEPO made by carbamylation of rhuEPO, possess tissue protective functions, but lack hematopoietic activity (Erbayraktar et al. 2003; Leist et al. 2004; Wang et al. 2004). Both of these EPO derivatives have been considered as potential novel neuroprotective and cardioprotective agents (Erbayraktar et al. 2003; Fiordaliso et al. 2005; Genc et al. 2004). In particular, asialo-rhuEPO has been well documented to have multiple cytoprotective functions (Calvillo et al. 2003; Erbayraktar et al. 2003; Wang et al. 2004) even though it has a very short plasma half-life (Erbayraktar et al. 2003). Moreover, asialo-rhuEPO can still cross the blood-brain barrier (BBB) and exert a neuroprotective effect in the central nervous system (Brines et al. 2000; Erbayraktar et al. 2003).

Asialo-rhuEPO is commercially unavailable. A small amount of asialo-rhuEPO can be prepared by removing sialic acid from commercially available rhuEPO using sialidase (Erbayraktar et al. 2003; WO2002/053580) or acidifying and heating process (US Patent Application Publication No. 20090005540). These approaches however, are not viable for large scale production of asialo-rhuEPO because of limited availability and high cost of rhuEPO. Human EPO has been expressed in insect cells (Kim et al. 2005; Quelle et al. 1989), bacterium (Lee-Huang 1984), yeast (Elliott et al. 1989) and plants (Cheon et al. 2004; Matsumoto et al. 1995), but rhuEPOs produced in these non-mammalian hosts are biologically inactive in vivo because of no or improper glycosylation. Since functional rhuEPO can be produced only in the mammalian cells with low expression level (Jacobs et al. 1985; Krantz 1991), its price is extremely high (~4,000 US$/mg) (Weise et al. 2007), which makes it unreasonable for asialo-rhuEPO production. The asialo-rhuEPO may also be produced by using a sialyltransferase deficient cell as a host cell (WO2002/053580). However, the method using a specific host cell has problems of low yield and high cost of cell culture, which makes this strategy impractical. Therefore, it is desirable to seek alternative ways to produce asialo-rhuEPO at a lower cost.

A plant-based expression system could be an attractive alternative for asialo-rhuEPO production. Firstly, plant expression systems offer many potential advantages, such as the same genetic codon usage as mammals, low cost, ease of scaling up in production and free of mammalian pathogens (Conrad and Fiedler 1998). Secondly and most importantly, plants can produce complex N-linked glycans although they are not identical to those from mammalian cells (Ma et al. 2003; Denecke et al. 1990; Edmund et al. 1998). The first few steps leading to the formation of oligomannosidic structures are conserved in both plants and mammals, but the later steps involved in the maturation of N-glycans are different (Lerouge et al. 1998). A mammalian glycoprotein produced in plants will have a plant specific β1, 2-xylose and a core α1,3-fucose (α1,6-fucose in mammals), while it will lack β 1,4-galactose and terminal sialic acid residues (Lerouge et al. 1998; Bakker et al. 2001; Ma et al. 2003). For the production of glycoproteins with human-like N-glycosylation, "ideal" plants would require knocking out genes encoding for β1,2-xylosyltransferase (XylT) and α1,3-fucosyltransferase (FucT), overexpression of a human GalT for addition of β 1,4-galactose and several other genes for the entire mammalian pathway for sialic acid biosynthesis and transfer (Gomord and Faye 2004; Edmund et al. 1998; Wee et al. 1998). Previous reports have shown that transgenic tobacco plants expressing GalT could produce recombinant antibodies with galactose-extended glycans similar to those produced in mammalian cell systems (Bakker et al. 2001, 2006; Palacpac et al. 1999; Misaki et al. 2003). The levels of β1,2-xylose and α1,3-fucose were reported to be undetectable in plant-produced antibodies. This is because human GalT competes for the acceptor substrate of both β1,2-XylT and α1,3-FucT (Palacpac et al. 1999) and that galactosylated glycans are poor substrates for both fucosyl- and xylosyltransferases (Zeng et al. 1997; Staudacher et al. 1995). Lack of ability of plants to sialylate N-glycans is a clear advantage for asialo-rhuEPO production.

Human EPO alone has been stably expressed in tobacco (Cheon et al. 2004; Conley et al. 2009; Musa et al. 2009) and *Arabidopsis* (Cheon et al. 2004) plants, tobacco cells (Matsumoto et al. 1995), and XylT and FucT double knockout moss (Weise et al. 2007) to produce asialoagalacto-rhuEPO, a EPO derivative lacking both sialic acid and galactose residues. Since β1,4-linked galactose residues are important for in vivo activity (Wasley et al.; 1991), plant-produced asialoagalacto-rhuEPO is likely to be biologically inactive in vivo for treating anemia. EPO has also been transiently expressed in XylT and FucT double knockdown *Nicotiana benthamiana* together with modified human genes encoding β1,4-mannosyl-β1,4-N-acetylglucosaminyltransferase, α1,3-mannosyl-β1,4-N-acetylglucosaminyltransferase and α1,6-mannosyl-β1,6-N-acetylglucosaminyltransferase to successfully produce EPO possessing bisected tetraantennary glycans (Castilho et al. 2011). Although many attempts have been made to express rhuEPO in plants (Matsumoto et al., 1995; Musa et al., 2009; Castilho et al., 2011), none of these studies were designed to develop tissue-protective rhuEPO derivatives. Conley et al. (2009) showed that crude protein extracts prepared from transgenic tobacco plants expressing rhuEPO protect kidney cells from injury. However, pure plant-produced rhuEPO was not isolated to confirm their findings and it was not clear whether the cytoprotective effect observed is indeed due to EPO or other tobacco proteins/metabolites.

Successful use of plant expression system for biopharmaceutical proteins not only depends on high expression levels of a target protein but also depends on efficient purification of recombinant proteins from plant cells and tissues. Since plants contain large amounts of chlorophyll, and phenolic compounds (Robic and Miranda, 2011), they cause serious problems for downstream bioprocessing. Ribulose 1,5-diphosphate carboxylase (RuBisCO) with molecular weight about 55 kD is an abundant protein in plants and comprises up to 25% of the total leaf proteins, which can mask recombinant proteins and make purification very difficult. Although several plant species have been used to produce asialoagalacto-rhuEPO by overexpressing human EPO gene alone, in only one case about 13.1 μg of EPO was purified from 6.3 kg transformed tobacco BY2 cells by means of immunoaffinity chromatography with an anti-EPO monoclonal antibody (Matsumoto et al., 1995). So far, there is no report on isolation rhuEPO from plant leaves. Therefore, establishing a workable purification system is important and necessary.

SUMMARY OF THE INVENTION

Methods are provided for the high-level production of asialoerythropoietin (asialo-rhuEPO) in a plant or plant cell comprising obtaining a transformed plant or transformed plant cell, wherein the transformed plant or transformed plant cell comprises a first promoter that drives expression in a plant cell operably linked to a first polynucleotide encoding human EPO fusion protein and a second promoter that drives expression in a plant cell operably linked to a second polynucleotide encoding a mammalian β1,4-galactosyltransferase, preferably a human β1,4-galactosyltransferase. The methods of the invention can further comprise making the transformed plant or transformed plant cell that comprises a first nucleic acid construct comprising the first promoter that drives expression in a plant cell operably linked to a first polynucleotide encoding human EPO fusion protein and a second nucleic acid construct comprising the second promoter that drives expression in a plant cell operably linked to a second polynucleotide encoding a mammalian β1,4-galactosyltransferase. The methods can further comprise growing the transformed plant or transformed plant cell under conditions favorable for the production of asialo-rhuEPO, whereby the transformed plant, the transformed plant cell, and/or plant part, plant cell, or seed of the transformed plant cell produces a relatively high level of asialo-rhuEPO.

Methods are provided for producing a plant or plant cell suitable for the production of asialo-rhuEPO. Such methods comprise introducing into a plant or plant cell a first nucleic acid construct comprising a first promoter that drives expression in a plant cell operably linked to a first polynucleotide encoding human EPO domain and a second nucleic acid construct comprising a second promoter that drives expression in a plant cell operably linked to a second polynucleotide encoding a mammalian β1,4-galactosyltransferase, preferably a human β1,4-galactosyltransferase.

Methods are provided for purifying asialo-rhuEPO from plant tissue. Such methods comprise at least one, but typically two, three or four, of the following steps: making an aqueous extract of leaves, wherein the plant tissue comprises asialo-rhuEPO; removing chlorophyll and/or RuBisCO protein from the aqueous extract; binding the asialo-rhuEPO in the aqueous extract to an immune affinity column or resin; and eluting the bound asialo-rhuEPO from the immune affinity column or resin.

Also provided are transformed plants and transformed plant cells that find use in the methods of the present invention for producing asialo-rhuEPO in plants and plant cells and for purifying such plant-produced asialo-rhuEPO. The transformed plants and transformed plant cells comprise stably incorporated in their genomes a first nucleic acid construct comprising a first promoter that drives expression in a plant cell operably linked to a first polynucleotide encoding human EPO and a second nucleic acid construct comprising a second promoter that drives expression in a plant cell operably linked to a second polynucleotide encoding a mammalian β1,4-galactosyltransferase. Further provided are plant parts, plant cells and seeds of the transformed plants that comprise first and/or second nucleic acid constructs as well as expression cassettes, nucleic acid constructs, polynucleotides, and plant-produced asialo-rhuEPO as disclosed herein.

fused with two tags StrepII and KDEL lies downstream of CaMV $35S^2$ promoter ($35S^2$ Pro), followed by nopaline synthase gene (nos) terminator (Nos Ter), whereas the GalT coding region (shown in purple) is flanked by a glyceralde-hydes-3-phosphate dehydrogease gene (GapC) promoter (GapC Pro) and terminator (GapC Ter). The expression construct also has a kanamycin-resistant neomycin phos-photransferase gene (nptII) (shown in blue) under control of nos promoter (Nos Pro). RB and LB stand for right and left borders, respectively.

Figure 2:
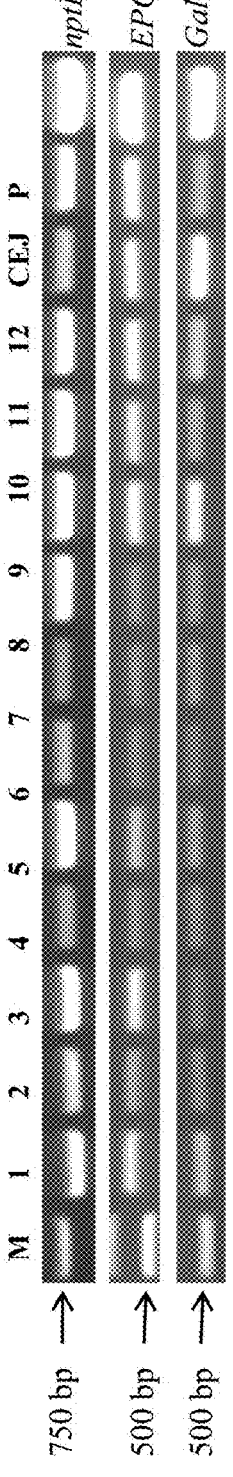

FIG. 2. PCR analysis to determine the presence of nptII, EPO and GalT in kanamycin-resistant tobacco plants. Genomic DNA obtained from leaves of kanamycin-resistant plants was used for PCR amplification with primers NptIIF/NptIIR, EPOPF/EPOPR and GalTF7/GalTR7. M, marker; P, plasmid carrying nptII, EPO and GalT, respectively; CEJ, transgenic control line CEJ120-12; 1-12, transgenic tobacco lines A56-1 to -12 expressing GalT and EPO.

Figure 3:
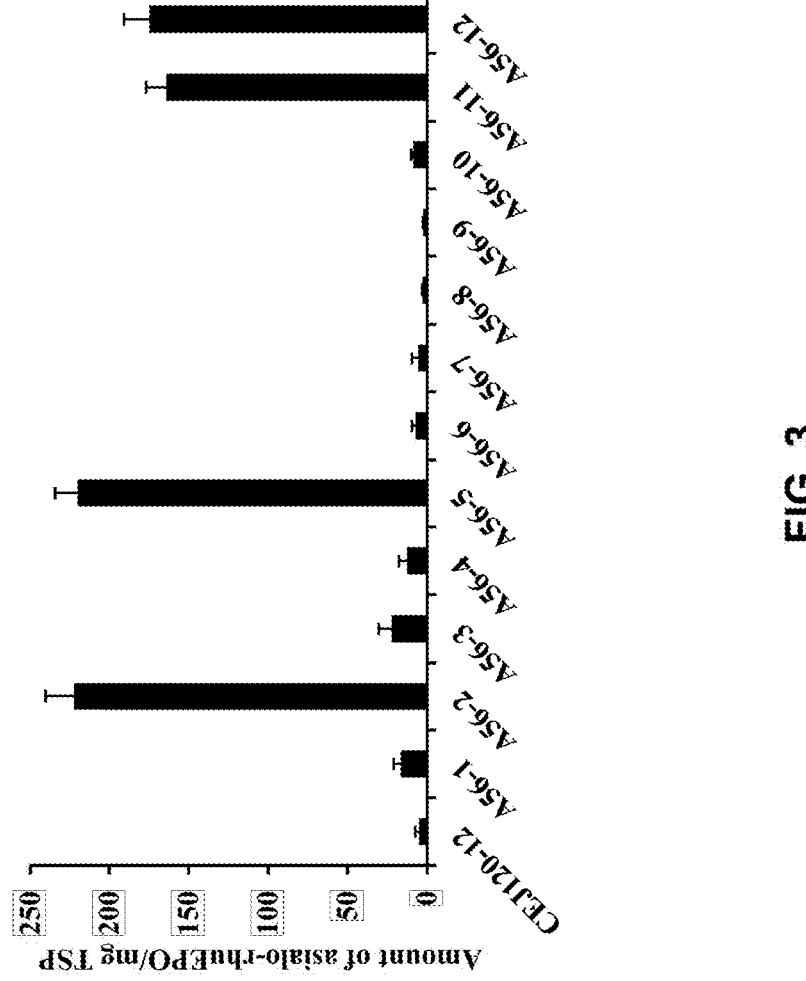

FIG. 3. Production level of asialo-rhuEPO in transgenic tobacco plants (A56-1 to -12) expressed under the control of a CaMV $35S^2$ promoter and with a C-terminal StrepII and KDEL fusion tags. Transgenic tobacco line CEJ120-12 expressing EPO under the control of a single CaMV 35S promoter and lacking a C-terminal fusion tag StrepII is shown as reference to indicate the influence of a CaMV $35S^2$ promoter and fusion tag on accumulation levels of asialo-rhuEPO in transgenic tobacco plants. The accumulation levels indicated in the FIG. are an average of three inde-pendent measurements ±SD.

Figure 4:
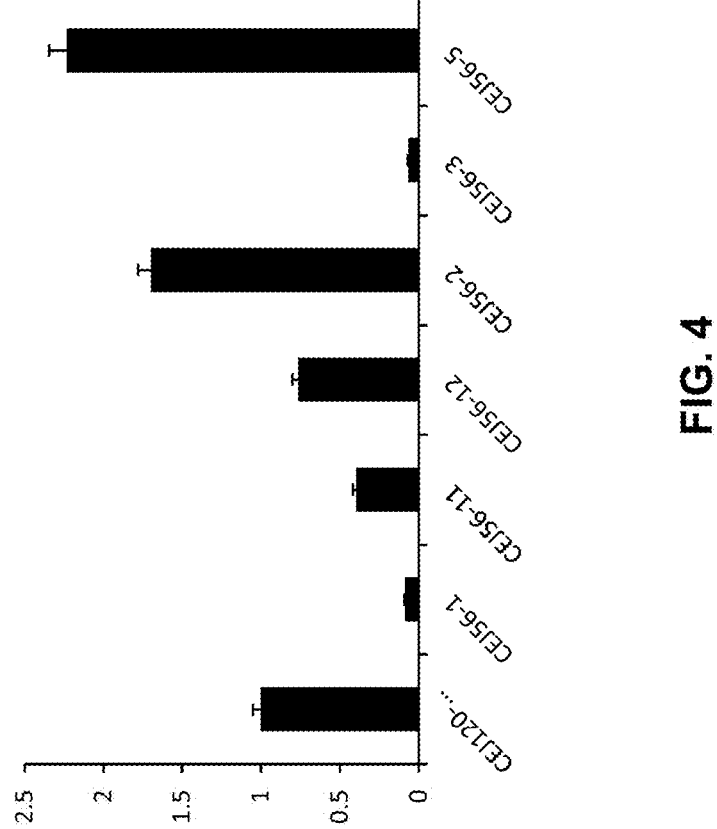

FIG. 4. QRT-PCR analysis of changes in transcript levels of EPO in selected transgenic tobacco lines (A56-1, A56-2, A56-3, A56-5, A56-11 and A56-12). Transgenic tobacco line CEJ120-12 expressing EPO under the control of a single CaMV 35S promoter was used as control. Data shown are fold changes calculated as transcript levels in A56 lines compared to control line CEJ120-12. Control line is defined as 1. Each assay was done in triplicate.

Figure 5:
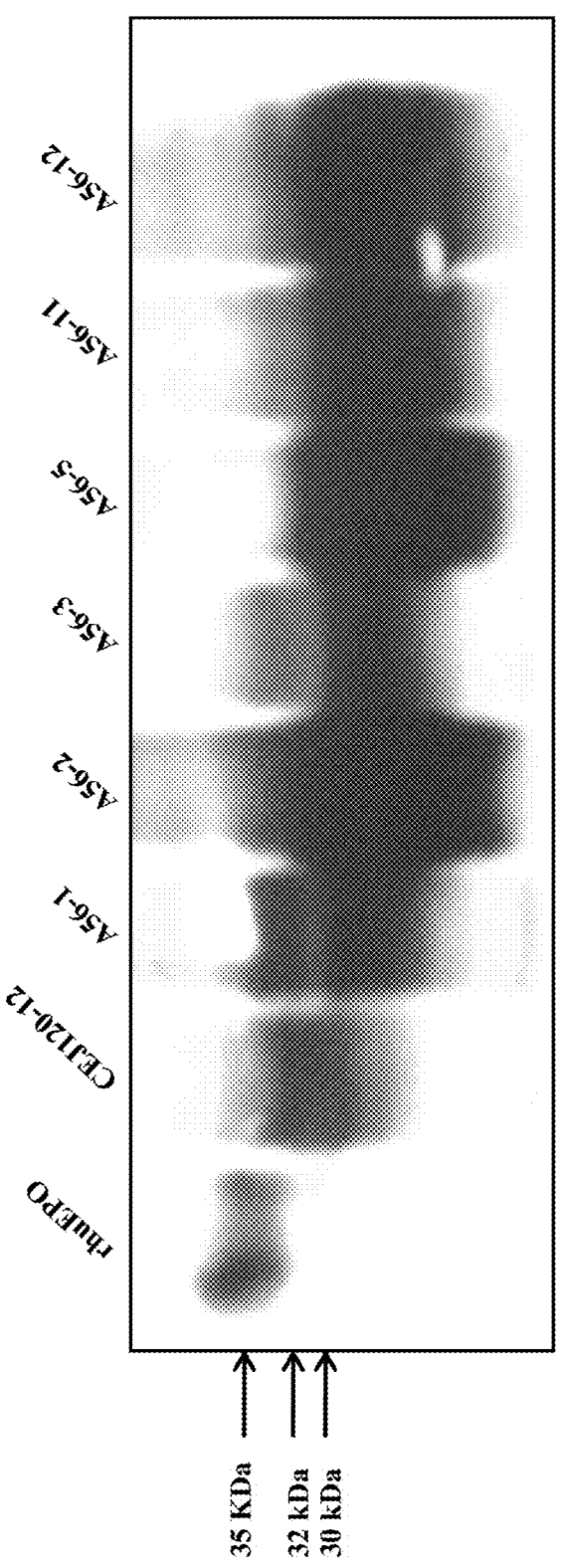

FIG. 5. Western blot analysis of asialo-rhuEPO in selected transgenic tobacco lines (A56-1, A56-2, A56-3, A56-5, A56-11 and A56-12) using anti-EPO specific antibody. Standard rhuEPO produced in CHO cells (lane 1) was used as positive control.

Figure 6:
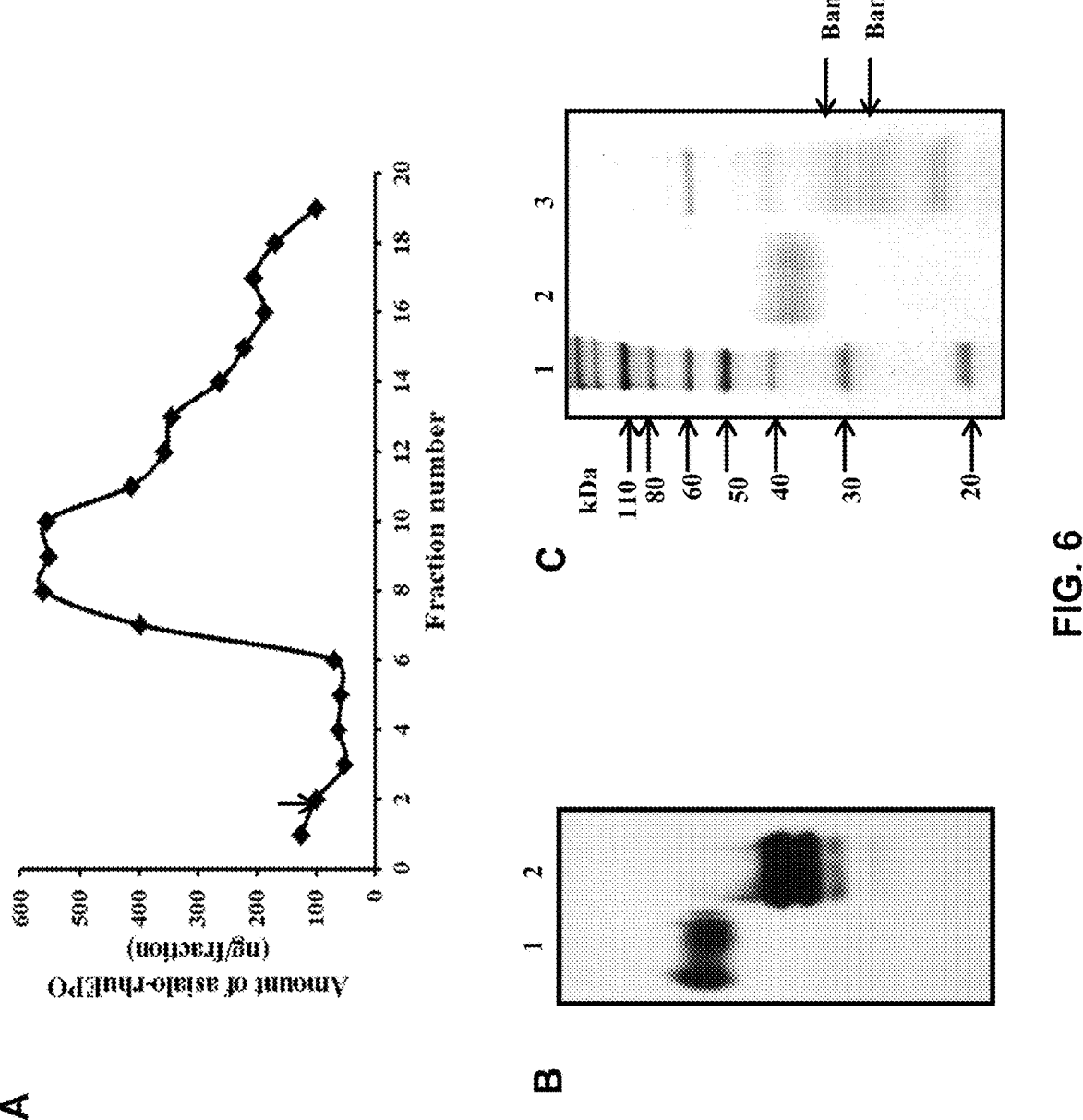

FIG. 6. A. IAC elution profile of asialo-rhuEPO from transgenic tobacco line A56-5. Bound asialo-rhuEPO was eluted with 0.1 M Glycine-HCl buffer, pH 2.5. The amount of asialo-rhuEPO in wash and elute fractions was deter-mined by sandwich ELISA and is shown as ng/fraction on Y-axis. The arrow in the panel indicates the start position of elution.

B. Western blot analysis of immunoaffinity purified plant-produced asialo-rhuEPO. Standard rhuEPO produced in CHO cells (lane 1) was used as positive control. Peak fractions (see FIG. 6A) were pooled and concentrated using a 10 kD cut-off centrifugal devise. About 0.5 μl of concentrated sample was mixed with 49.5 μl PBS, denatured and applied onto the gel.

C. SDS-PAGE profile of immunoaffinity purified asialo-rhuEPO. Peak fractions were pooled and concentrated using a 10 kD cut-off centrifugal devise. After removal of residual BSA using Melon Gel kit, about 7.0 μg of purified protein (lane 3) was loaded onto a 12.5% SDS-PAGE gel. RhuEPO produced in CHO cells (4 μg, lane 2) was also applied. After electrophoresis, the gel was stained with coomassie blue. Protein bands (band 1 and 2) corresponding to asialo-rhuEPO (indicated by arrows, lane 3) were excised for peptide mapping.

Figure 7:
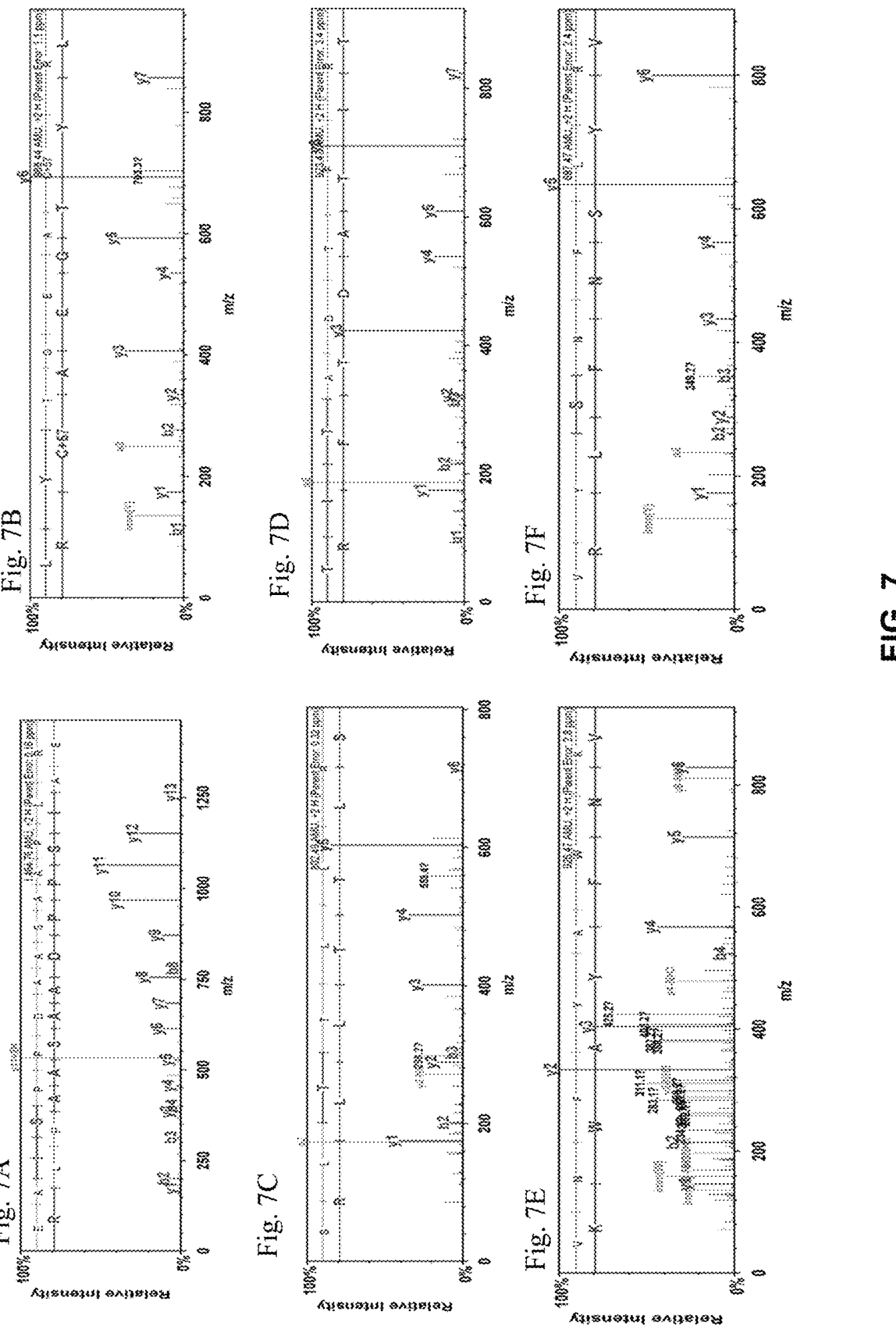

FIG. 7. MS/MS spectra of tryptic peptides of band 1 and their deduced amino acid sequences. Protein band 1 corre-sponding to asialo-rhuEPO (FIG. 6C, lane 3) was excised and subjected to protein identification by LC-MS/MS. FIGS. 7A-7F: MS/MS spectra of tryptic peptides and their deduced amino acid sequences.

FIG. 8. Identified peptide sequences in band 1 by LC-MS/MS. Identified peptides in band 1 (FIG. 6C, lane 3) are highlighted in red in their corresponding positions in human EPO polypeptide chain (Amino acids 28-193 of SEQ ID NO: 4).

Figures 9, 9A, 9B, 9C, 9D, 9E, 9F, 9G:
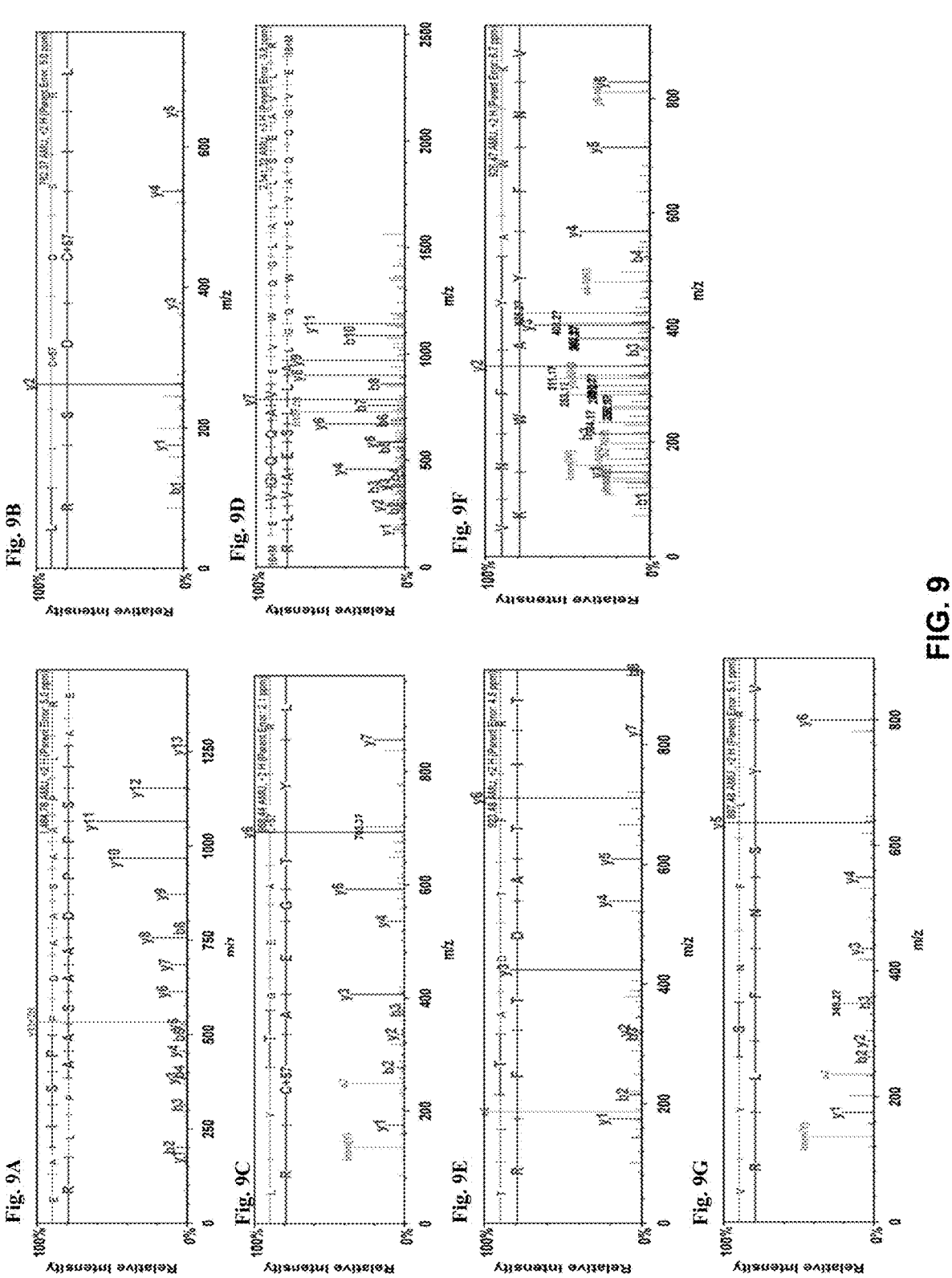

FIG. 9. MS/MS spectra of tryptic peptides of band 2 and their deduced amino acid sequences. Protein band 2 corre-sponding to asialo-rhuEPO (FIG. 6C, lane 3) was excised and subjected to protein identification by LC-MS/MS. FIG. 9A-9G: MS/MS spectra of tryptic peptides and their deduced amino acid sequences.

FIG. 10. Identified peptide sequences in band 2 by LC-MS/MS. Identified peptides in band 2 (FIG. 6C, lane 3) are highlighted in red in their corresponding positions in human EPO polypeptide chain (Amino acids 28-193 of SEQ ID NO: 4).

Figure 11:
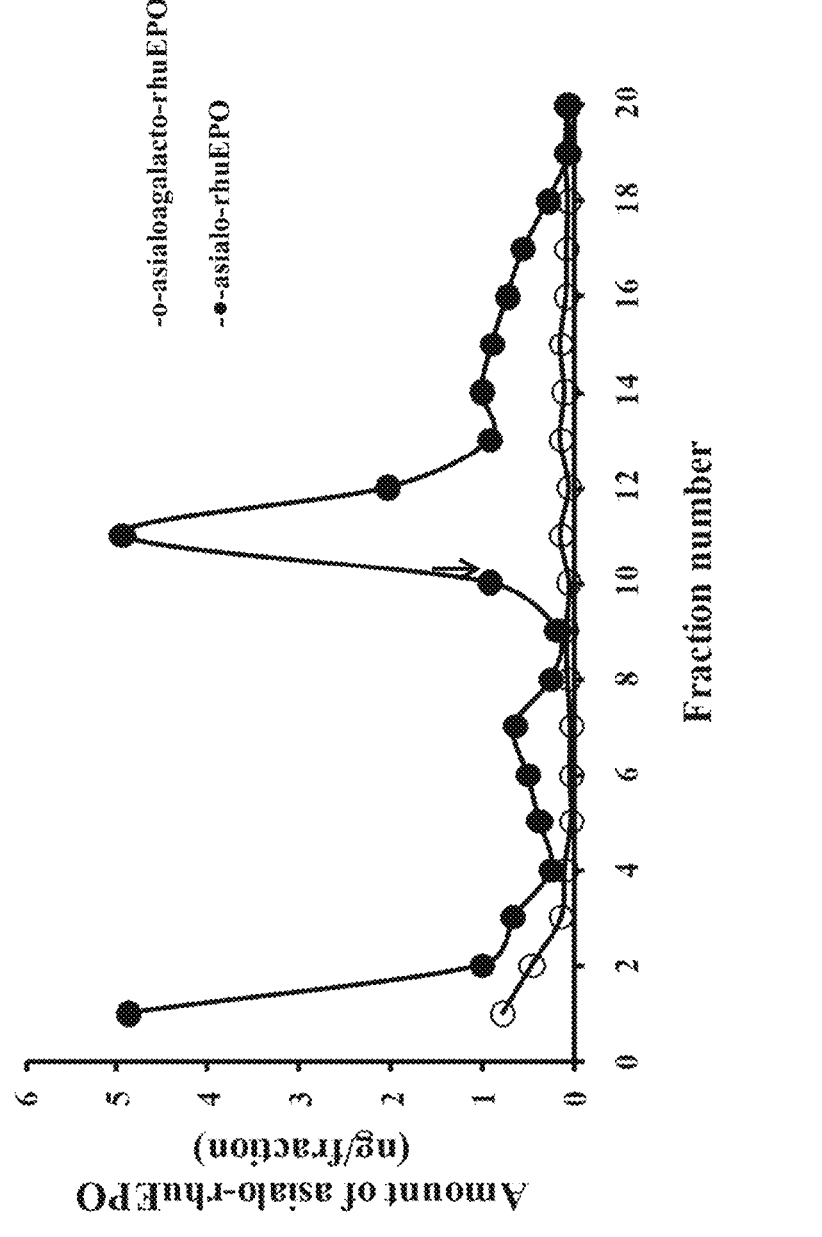

FIG. 11. Binding profile of asialo-rhuEPO to β1,4-galac-tose specific ECA-agarose lectin column. Purified asialo-rhuEPO (140 ng, 0.5 ml) was diluted with binding buffer (20 mM HEPES-KOH buffer, pH 7.3 containing 5 mM MgCl2 and 100 mM NaCl) and the resulting solution was incubated with ECA-agarose resin (1 ml) overnight at 4° C. Same amount of asialoagalacto-rhuEPO purified from transgenic tobacco line EPO9 expressing EPO alone was used as a negative control. Following binding, the resin was packed into column, washed with binding buffer (10 CV), and bound asialo-rhuEPO was eluted with 0.2 M lactose in binding buffer. Amount of bound and unbound plant-pro-duced EPO in wash and eluted fraction was determined using sandwich ELISA, and is expressed as ng/fraction as shown on the Y-axis.

Figure 12:
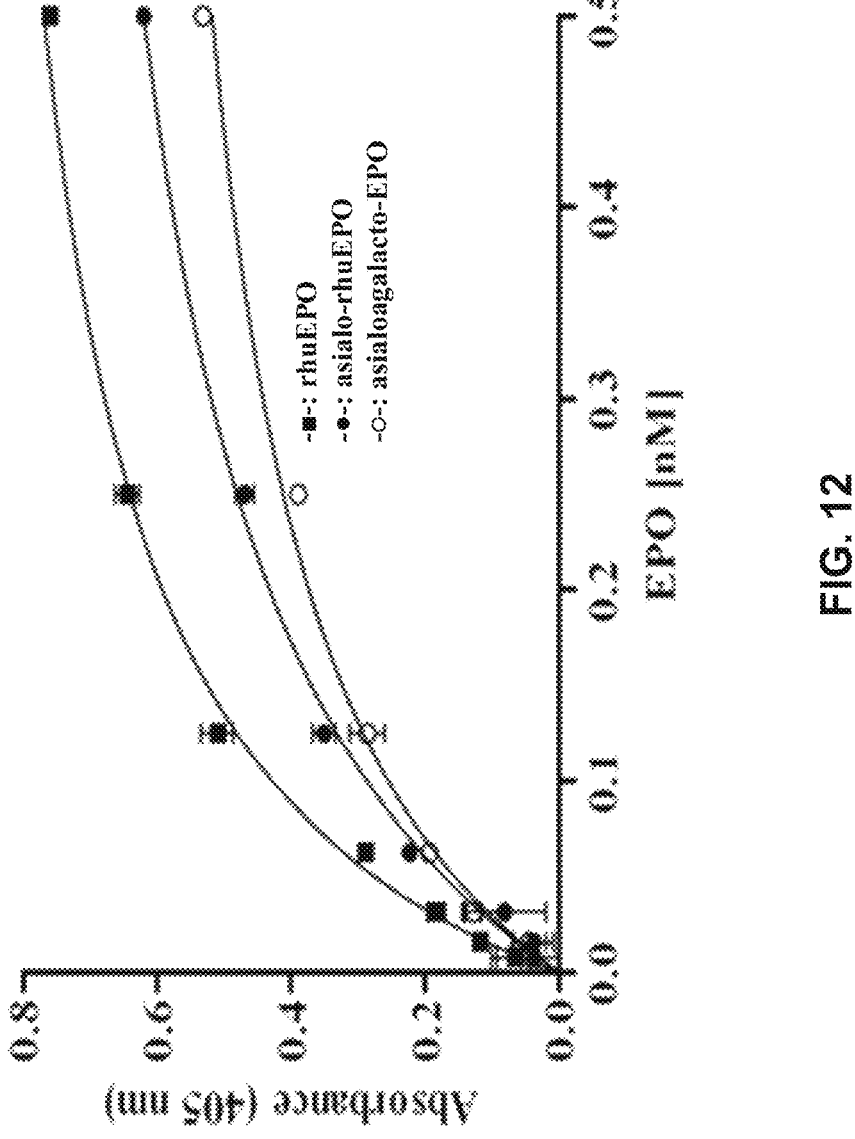

FIG. 12. Binding isotherm of asialo-rhuEPO to EPOR. Serial dilutions (0.5-0.0078 nM) of various EPOs were incubated with soluble EPOR receptor on ice for 15 min. The mixture was then applied onto an anti-EPOR antibody coated 96-well plate. Bound EPO was detected using rabbit anti-EPO antibody. Data presented in the figure are mean of three replicates ±SD. Experiment was repeated once.

Figure 13:
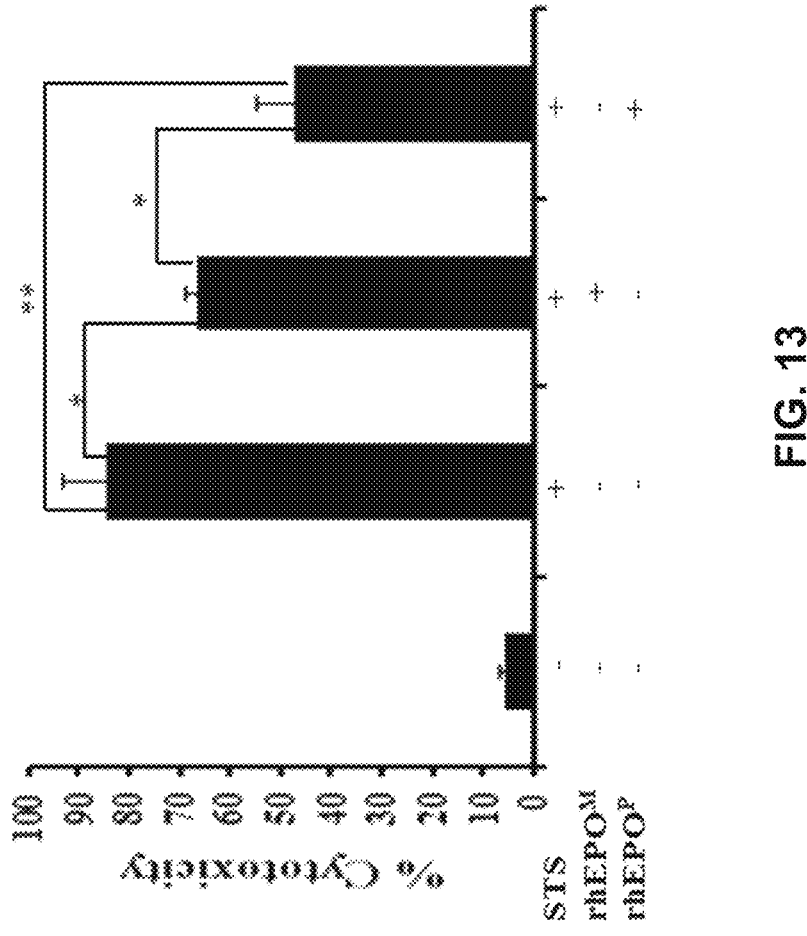

FIG. 13. Cytoprotective effect of plant-produced asialo-rhEPO on the staurosporine (STS)-induced cytotoxicity in N2A cells. Cells were simultaneously treated with 1 μM STS and 20 U/ml plant-produced asialo-rhEPO (asialo-rhEPO$^P$) or CHO-produced rhEPO (rhEPO$^M$, positive control) for 12 hrs. The cytotoxicity was measured by LDH assay and % cytotoxicity values from three independent experiments, each involving six replicates are presented in the histogram. * and **: p<0.05 and 0.01.

Figure 14:
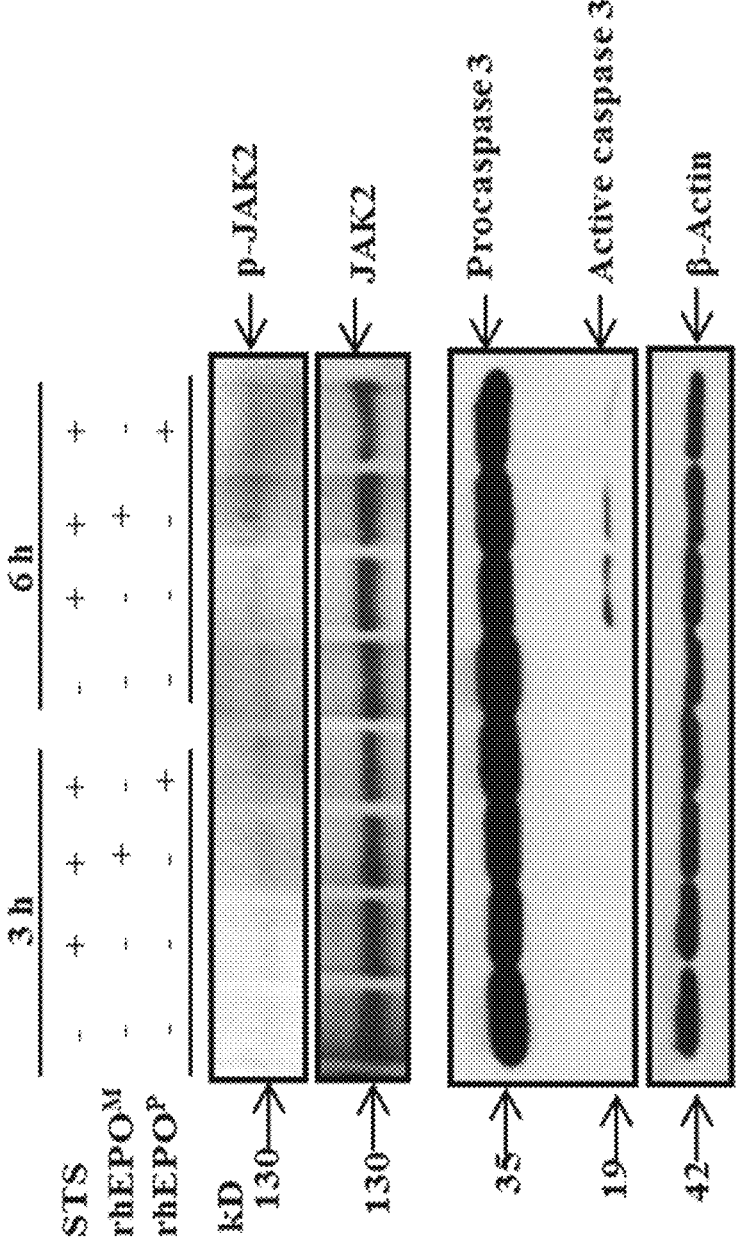

FIG. 14. Western blot analysis of p-JAK2/JAK2 and active caspase 3 in lysates of N2A cells simultaneously treated with 20 U/ml plant-produced asialo-rhEPO (asialo-rhEPO$^P$) or CHO-produced rhEPO (rhEPO$^M$) and 1 μM STS for 3 and 6 hrs, respectively. Untreated control and STS treated cell lysates were also included in the analysis. For JAK2, about 50 μg of protein was applied per lane on a 7.5% SDS-PAGE gel. The blot was probed with anti-p-JAK antibody. Then the blot was stripped and re-probed with anti-total JAK2 antibody. For active caspase 3 detection, about 40 μg of protein was applied on a 12.5% SDS-PAGE gel. Following protein transfer, both inactive procaspase 3 and active caspase 3 was revealed by probing the blot with rabbit anti-caspase 3 antibody. The protein level of R-actin was used as internal control.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus. The nucleotide sequences disclosed herein that are coding sequences may or may not comprise stop codons at the end of the coding. It is recognized that such stop codons can be added in the same reading frame as a coding sequence to stop translation at the codon immediately before the stop codon. The present invention does not depend on the use of a particular stop codon. Any stop codon can be used including, for example, TAA, TAG, and TGA.

SEQ ID NO: 1 sets forth a nucleic acid sequence encoding an asialo-rhuEPO fusion protein.

SEQ ID NO: 2 sets forth the amino acid sequence of the asialo-rhuEPO fusion protein encoded by SEQ ID NO: 1.

SEQ ID NO: 3 sets forth a nucleic acid sequence encoding a human EPO.

SEQ ID NO: 4 sets forth the amino acid sequence of the human EPO encoded by SEQ ID NO: 3.

SEQ ID NO: 5 sets forth the amino acid sequence of the tobacco etch virus (TEV) cleavage domain.

SEQ ID NO: 6 sets forth the amino acid sequence of the StrepII tag domain.

SEQ ID NO: 7 sets forth the amino acid sequence of one endoplasmic reticulum (ER) retention signal domain.

SEQ ID NO: 8 sets forth the amino acid sequence of another ER retention signal domain.

SEQ ID NO: 9 sets forth the nucleic acid sequence of the double CaMV 35S promoter.

SEQ ID NO: 10 sets forth a nucleic acid sequence encoding a human β1,4-galactosyltransferase.

SEQ ID NO: 11 sets forth the amino acid sequence of the human β1,4-galactosyltransferase encoded by SEQ ID NO: 10.

SEQ ID NO: 12 sets forth the nucleic acid sequence of the tobacco GapC promoter.

SEQ ID NO: 13 sets forth the nucleic acid sequence of the tobacco GapC terminator.

SEQ ID NO: 14 sets forth an artificial sequence for the primer EPOPF.

SEQ ID NO: 15 sets forth an artificial sequence for the primer EPOPR.

SEQ ID NO: 16 sets forth an artificial sequence for the primer GalTF.

SEQ ID NO: 17 sets forth an artificial sequence for the primer GalTR.

SEQ ID NO: 18 sets forth an artificial sequence for the primer NptIIPF.

SEQ ID NO: 19 sets forth an artificial sequence for the primer NptIIPR.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. Additional embodiments of the invention are described in the Appendix.

The present invention discloses the engineering of the N-glycosylation pathway in plants, particularly tobacco (Nicotiana tabacum) plants, to produce asialo-rhuEPO. While specific embodiments of the invention describe tobacco plants engineered to produce asialo-rhuEPO, the present invention is not limited to Nicotiana tabacum or even to other species in the genus Nicotiana, such as, for example, N. benthamiana but is broadly applicable to other plant species including, but not limited to, monocots and dicots.

As disclosed herein, the present invention provides a methods and a plant expression system for the production of a recombinant human erythropoietin (rhuEPO) derivative, asialoerythropoietin (asialo-rhuEPO). The methods find use in the high level of production of asialo-rhuEPO that is suitable for the commercial production of asialo-rhuEPO. In certain embodiments of the invention, the asialo-rhuEPO comprises asialo-rhuEPO fusion protein, which comprises a human EPO domain and at least one additional domain. As disclosed hereinbelow, asialo-rhuEPO fusion protein that is produced by the methods and plants of the present invention is a tissue protective cytokine that yields cytoprotective effects that are superior to mammalian-produced rhuEPO. Thus, the present invention finds use in the production of asialo-rhuEPO for use as a therapeutic agent that promotes tissue protective functions. Moreover, the methods of the present invention for producing asialo-rhuEPO are less expensive than existing methods of production. If desired, the one or more additional domains of an asialo-rhuEPO fusion protein of the present invention can be removed as described hereinbelow.

The present invention provides methods for the production and purification for asialo-rhuEPO, method for producing a plant or plant cell suitable for the production of asialo-rhuEPO, transformed plants and transformed plant cells made by such methods, and method for treatment of a human individual with asialo-rhuEPO that is produced and purified by the methods disclosed herein. As used herein unless apparent from the context of usage, "asialo-rhuEPO" is intended to encompass all forms of asialo-rhuEPO that are produced by the methods and transformed plants and transformed plants cells disclosed herein. Such forms of asialo-rhuEPO include, but are not limited to, asialo-rhuEPO fusion proteins produced by the methods and transformed plants and transformed plants cells disclosed herein and derivatives of such asialo-rhuEPO fusion proteins comprising at least the human EPO domain.

By "asialo-rhuEPO fusion protein" is intended a fusion protein comprising a human EPO domain operably linked to at least one additional domain including, but not limited to, a protease cleavage domain, a tag domain, and an endoplasmic reticulum (ER) retention signal domain. In some embodiments, the asialo-rhuEPO fusion protein comprises in operable linkage a human EPO domain, a protease cleavage domain, a tag domain, and an ER retention signal domain. In preferred embodiments, asialo-rhuEPO fusion protein comprises in operable linkage and in the following order from N-terminal to C-terminal end, a human EPO domain, a protease cleavage domain, a tag domain, and an ER retention signal domain. In more preferred embodiments, the asialo-rhuEPO fusion protein comprises in operable linkage and in the following order from N-terminal to C-terminal end, a human EPO domain, TEV protease cleavage domain, a StrepII tag domain, and a KDEL (SEQ ID NO: 7) ER retention signal domain.

Derivatives of an asialo-rhuEPO fusion protein of the present invention include, for example, asialo-rhuEPO lacking one, two, three or all of the additional domains described herein. Such derivatives can be prepared, for example, through the enzymatic cleavage at cleavage site in an asialo-rhuEPO fusion protein of the present. For example, in certain embodiments of the invention, the asialo-rhuEPO fusion protein comprises on the C-terminal of the human EPO domain side the following additional domains in an N-terminal to C-terminal order: a TEV cleavage domain, a StrepII domain, and KDEL ER retention domain. A derivative of such an asialo-rhuEPO fusion protein can be produced, for example, by the incubating the asialo-rhuEPO fusion protein in the presence of an effective amount of TEV protease by standard methods that are known in the art. The derivative produced thereby will comprise the human EPO domain but lack the additional domains. It is recognized that that derivative can comprise one or more additional amino acids on the C-terminal end that remain after cleavage at the TEV cleavage domain.

By "human erythropoietin fusion protein" or "human EPO fusion protein" is intended to mean a fusion protein comprising a human EPO domain, which comprises the amino acid sequence of a human EPO. Preferably, the human EPO domain comprises the amino acid sequence set forth in SEQ ID NO: 4 or disclosed in Accession No. NP_000799. Such a "human erythropoietin fusion protein" or "human EPO fusion protein" can further comprise at least one of the additional domains that are described above.

The present invention provides methods for the high-level production of asialoerythropoietin (asialo-rhuEPO) in a plant or plant cell and transformed plants and plant cells that can be used in such methods. By "high-level production of asialo-rhuEPO" is intended to mean that asialo-rhuEPO is produced at a high level in a plant, plant cell, plant organ, other plant part, or seed. Preferably, the high level of asialo-rhuEPO is at least about 50, 75, 100, 125, 150, 175, 200, 225, 250 or more ng asialo-rhuEPO per mg of total soluble protein in an aqueous extract prepared from plant tissues. Suitable methods for preparing an aqueous protein extract from plant tissues and for determining the total soluble protein concentration in such a protein extract are described below in the Example or otherwise known in the art.

The methods for the high-level production of asialo-rhuEPO comprise obtaining a transformed plant or transformed plant cell that comprises a first promoter that drives expression in a plant cell operably linked to a first polynucleotide encoding a human erythropoietin (EPO) fusion protein and a second promoter that drives expression in a plant cell operably linked to a second polynucleotide encoding a β1,4-galactosyltransferase. The methods can further comprise growing the transformed plant or transformed plant cell under conditions favorable for the production of asialo-rhuEPO, whereby the transformed plant, plant part, plant cell, or seed thereof or the transformed plant cell produces a high level of asialo-rhuEPO. If desired, the methods for the high-level production of asialo-rhuEPO can further comprise one or more additional steps for making the transformed plant or transformed plant cell and/or one or more additional steps for purification of the asialo-rhuEPO as disclosed hereinbelow.

The present invention further provides methods for producing a plant or plant cell suitable for the production of asialo-rhuEPO, particularly by suitable for the production of asialo-rhuEPO by the methods of the present invention. The methods for producing a plant or plant cell suitable for the production of asialo-rhuEPO comprising introducing into a plant or plant cell a first nucleic acid construct comprising a first promoter that drives expression in a plant cell operably linked to a first polynucleotide encoding a human EPO fusion protein and a second nucleic acid construct comprising a second promoter that drives expression in a plant cell operably linked to a second polynucleotide encoding a mammalian β1,4-galactosyltransferase. In some embodiments of the invention, the first and second nucleic acid constructs are in separate expression cassettes and are introduced into the plant or plant cell by simultaneously or sequentially by a plant transformation method disclosed herein or otherwise known in the art. Alternatively, a plant or plant cell comprising both the first and second nucleic acid constructs can be produced crossing a first plant comprising the first nucleic acid construct with a second plant comprising the second nucleic acid construct and selecting for progeny plants and cells thereof that comprise both the first and second nucleic acid constructs. The first plant can be produced by introducing the first nucleic acid construct into the first plant by, for example, a stable transformation. Likewise, the second plant can be produced by introducing the second nucleic acid construct into the second plant by, for example, a stable transformation. Methods of stable transformation are disclosed hereinbelow and are generally known in the art.

Figure 1:
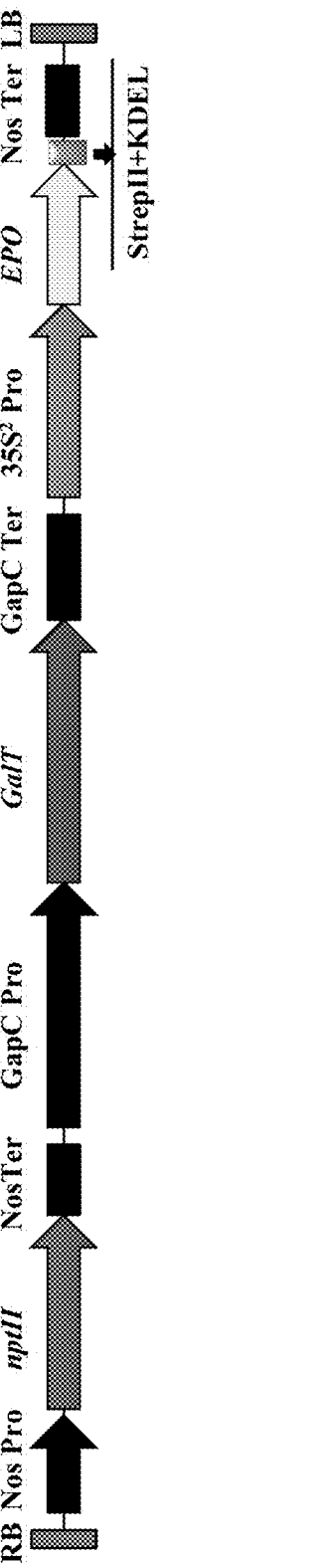
FIG. 1. Schematic representation of the plant expression cassette A56. The EPO coding region (shown in yellow)

In other embodiments, an expression cassette comprising both the first and second nucleic acid constructs can be introduced into a plant or plant cell. An example of a preferred expression cassette comprising both the first and second nucleic acid constructs is depicted in FIG. 1.

In the methods of the present invention, nucleic acid constructs, expression cassettes, or polynucleotides are introduced into at least one cell of a plant using any method known in the art or disclosed herein. Such methods include, for example, stable and transient transformation methods. By "stable transformation" is intended to mean that the nucleic acid construct, expression cassette, or polynucleotide that is introduced into at least one plant cell is incorporated into a genome of the transformed plant cell whereby the nucleic acid construct, expression cassette, or polynucleotide is inherited by subsequent cells that are derived from the transformed cell and/or by progeny plants that are derived from a transformed plant that was produced from the transformed plant cell. By "transient transformation" is intended to mean that the nucleic acid construct, expression cassette, or polynucleotide that is introduced into at least one plant cell is not incorporated into a genome of the plant cell or thus, is not expected to be inherited by progeny cells and progeny plants derived therefrom.

Methods of the present invention can involve the use of a first polynucleotide encoding a human EPO fusion protein. Such a first polynucleotide encodes a human EPO fusion protein comprising a human EPO domain and preferably, at least one additional domain. In particular, the first polynucleotide comprises a nucleic acid sequence encoding a human EPO fusion protein and optionally one or more operably linked nucleic acid sequences each encoding an additional domain. The additional can include, but at not limited to, a protease cleavage domain, a tag domain, and an ER retention signal domain. In one embodiment of the invention, the first polynucleotide encodes a human EPO fusion protein comprising in operable linkage a human EPO domain operably linked to an ER retention signal domain, preferably the ER retention domain comprising the amino acid sequence set forth in SEQ ID NO: 7. In another embodiment of the invention, the first polynucleotide encodes a human EPO fusion protein comprising in operable linkage a human EPO domain, a protease cleavage domain, a tag domain, and an ER retention signal domain. In a yet another embodiment of the invention, the first polynucleotide encodes a human EPO fusion protein comprising in operable linkage and in an N-terminal to C-terminal direction, a human EPO domain, a protease cleavage domain, a tag domain, and an ER retention signal domain. In a preferred embodiment of the invention, the first polynucleotide encodes a human EPO fusion protein comprising in operable linkage and in an N-terminal to C-terminal direction, a human EPO domain, a TEV cleavage domain, a StrepII tag domain, and a KDEL (SEQ ID NO: 7) ER retention signal domain. In a more preferred embodiment of the invention, the first polynucleotide encodes a human EPO fusion protein comprising in operable linkage and in an N-terminal to C-terminal direction, a human EPO domain comprising the amino acid sequence set forth in SEQ ID NO: 4 or the amino acid sequence encoded by SEQ ID NO: 3, a TEV cleavage domain comprising the amino acid sequence set forth in SEQ ID NO: 5, a StrepII tag domain comprising the amino acid sequence set forth in SEQ ID NO: 6, and a KDEL (SEQ ID NO: 7) ER retention signal domain comprising the amino acid sequence set forth in SEQ ID NO: 7. In a even more preferred embodiment of the invention, the first polynucleotide comprises the nucleic acid sequence set forth in SEQ ID NO: 1 or a nucleic acid encoding SEQ ID NO: 2.

Although certain protease cleavage domains, tag domains, and ER retention signal domains are disclosed herein, it is recognized that other suitable cleavage domains, tag domains, and ER retention signal domains and nucleic acid molecules encoding them are known in the art and can be used in methods disclosed herein. Thus, the use of such other suitable cleavage domains, tag domains, and ER retention signal domains and the nucleic acid molecules encoding are encompassed by the present invention Methods of the present invention can involve the use of a second polynucleotide comprising a nucleic acid sequence encoding a β1,4-galactosyltransferase, preferably a β1,4-galactosyltransferase that can add β1,4-galactose to N-glycan chain attached to protein when such a β1,4-galactosyltransferase is expressed in a plant or plant cell, more preferably a β1,4-galactosyltransferase that can add β1,4-galactose to N-glycan chain of asialo-rhuEPO when such a β1,4-galactosyltransferase is expressed in a plant or plant cell comprising rhuEPO. β1,4-galactosyltransferases that can be used in the present invention include, for example, mammalian β1,4-galactosyltransferases, particularly human β1,4-galactosyltransferases. A preferred β1,4-galactosyltransferase comprises the amino sequence set forth in SEQ ID NO: 11 or an amino sequence encoded by SEQ ID NO: 10. A preferred second polynucleotide of the present invention comprises the nucleic acid sequence set forth in SEQ ID NO: 10 or a nucleic acid sequence encoding SEQ ID NO: 11.

The invention further provides methods for purifying asialo-rhuEPO from plant tissue. While such methods are particularly suited for use with plant tissue from plants that are produced the methods of the present invention, the methods are suitable for purifying asialo-rhuEPO from any plant tissue, plant part, plant organ, or plant cell that produces asialo-rhuEPO. The plant tissue can be, for example, leaf, stem, root, fruit, flower, and/or seed tissue or even a cultured plant tissues or cells as long as the plant tissue comprises asialo-rhuEPO. Preferably, however, the plant tissue comprises leaves. More preferably, the plant tissue comprises leaves from a plant that has been produced by the methods disclosed herein for producing a plant suitable for the production of asialo-rhuEPO. Most preferably, the plant tissue comprises leaves from a transgenic tobacco plant that has been produced by the methods disclosed herein for producing a plant suitable for the production of asialo-rhuEPO. In preferred embodiments of the method, the plants that are the source of the leaves are grown under conditions favorable for the production of asialo-rhuEPO before the leaves were harvested.

The methods for purifying asialo-rhuEPO comprise making an aqueous extract of plant tissue that comprises asialo-rhuEPO. Typically, making an aqueous extract of plant tissue will comprise the use of an appropriate extraction solution comprising a standard buffer such as, for example, phosphate-buffered saline (PBS) or Tris-HCl at a suitable pH typically about from about pH 6.8 to 7.5, preferably about pH 7.3. The methods further can further comprise the step of removing chlorophyll and/or RuBisCO protein from the aqueous extract, particularly if the plant tissue is green. The methods can further comprise the steps of binding the asialo-rhuEPO in the aqueous extract to an immune affinity column and eluting the bound asialo-rhuEPO from the immune affinity column so as to produce purified asialo-rhuEPO.

The present invention further provides a method of treatment comprising administering to a human individual an effective amount of plant-produced asialo-rhuEPO. The effective amount of asialo-rhuEPO that is administered to the individual is an amount of the asialo-rhuEPO that has been determined to provide a tissue protective effect to at least one human individual. Those of skill in the art understand that an effective amount of asialo-rhuEPO for a tissue protective effect can be determined, for example, by administering a range of amounts of asialo-rhuEPO to one or more human individuals at one time or at multiple time and then determining the amount (i.e., the effective amount) produces the desired tissue protective effect in a human individual, put preferably without causing any undesired cytotoxic or other deleterious effects. Such an effective amount can be single amount (e.g., 0.5 mg/day) but will typically be a range (e.g., 0.5-2.5 mg/day) and/or comprise multiple doses (e.g., 0.5-2.5 mg/day for each of 5 consecutive days, or 0.5 mg/day two times per day for two weeks).

In preferred embodiments of the method of treatment, asialo-rhuEPO is produced in a plant made by the methods of the present invention. In more preferred embodiments, asialo-rhuEPO is produced in plants made by the methods of the present invention and purified by the methods of the present invention.

Further embodiments of the invention include, but are not limited to, the following:

1. A method for the high-level production of asialoerythropoietin (asialo-rhuEPO) in a plant or plant cell comprising obtaining a transformed plant or transformed plant cell, wherein the transformed plant or transformed plant cell comprises a first promoter that drives expression in a plant cell operably linked to a first polynucleotide encoding a human erythropoietin (EPO) fusion protein and a second promoter that drives expression in a plant cell operably linked to a second polynucleotide encoding a β1,4-galactosyltransferase.

2. The method of embodiment 1, wherein the human EPO fusion protein comprises a human EPO domain and further comprises at least one operably linked additional domain selected from the group consisting of a protease cleavage domain, a tag domain, and an endoplasmic reticulum (ER) retention signal domain.

3. The method of embodiment 1 or 2, wherein the human EPO fusion protein further comprises in operable linkage a protease cleavage domain, a tag domain, and ER retention signal domain.

4. The method of any one of embodiments 1-3, wherein the human EPO fusion protein comprises in operable linkage and in an N-terminal to C-terminal direction, a human EPO domain, a protease cleavage domain, a tag domain, and an ER retention signal domain.

5. The method of any one of embodiments 2-4, wherein the protease cleavage domain is the tobacco etch virus (TEV) cleavage domain.

6. The method of embodiment 5, wherein the TEV cleavage domain comprises the amino acid sequence set forth in SEQ ID NO: 5.

7. The method of any one of embodiments 2-6, wherein the tag domain is a StrepII tag domain.

8. The method of embodiment 7, wherein the StrepII tag domain comprises the amino acid sequence set forth in SEQ ID NO: 6.

9. The method of any one of embodiments 2-8, wherein the ER retention signal domain comprises the amino acid sequence set forth in SEQ ID NO: 7.

10. The method of any one of embodiments 2-8, wherein the ER retention signal domain comprises the amino acid sequence set forth in SEQ ID NO: 8.

11. The method of any one of embodiments 2-10, wherein the human EPO domain comprises an amino acid sequence selected from the group consisting of:
   (a) the amino acid sequence set forth in SEQ ID NO: 4; and
   (b) the amino acid sequence encoded by the nucleic acid sequence set forth in SEQ ID NO: 3.

12. The method of any one of embodiments 2-11, wherein the human EPO domain is encoded by a nucleic acid sequence selected from the group consisting of:
   (a) the nucleic acid sequence set forth in SEQ ID NO: 3; and
   (b) a nucleic acid sequence encoding the amino acid sequence set forth in SEQ ID NO: 4.

13. The method of any one of embodiments 1-12, wherein the human EPO fusion protein comprises an amino acid sequence selected from the group consisting of:
   (a) the amino acid sequence set forth in SEQ ID NO: 2; and (b) the amino acid sequence encoded by the nucleic acid sequence set forth in SEQ ID NO: 1.

14. The method of any one of embodiments 1-13, wherein the first polynucleotide comprises a nucleic acid sequence selected from the group consisting of:
   (a) the nucleic acid sequence set forth in SEQ ID NO: 1; and
   (b) a nucleic acid sequence encoding the amino acid sequence set forth in SEQ ID NO: 2.

15. The method of any one of embodiments 1-14, wherein the β1,4-galactosyltransferase is a mammalian β1,4-galactosyltransferase.

16. The method of any one of embodiments 1-15, wherein the β1,4-galactosyltransferase is a human β1,4-galactosyltransferase.

17. The method of any one of embodiments 1-16, wherein the β1,4-galactosyltransferase comprises an amino acid sequence selected from the group consisting of:
   (a) the amino acid sequence set forth in SEQ ID NO: 11; and
   (b) the amino acid sequence encoded by the nucleic acid sequence set forth in SEQ ID NO: 10.

18. The method of any one of embodiments 1-16, wherein the second polynucleotide comprises a nucleic acid sequence selected from the group consisting of:
   (a) the nucleic acid sequence set forth in SEQ ID NO: 10; and
   (b) a nucleic acid sequence encoding the amino acid sequence set forth in SEQ ID NO: 11.

19. The method of any one of embodiments 1-18, further comprising making the transformed plant or transformed plant cell, wherein the transformed plant or transformed plant cell comprises a first nucleic acid construct comprising the first promoter operably linked to the first polynucleotide and a second nucleic acid construct comprising the second promoter operably linked to the second polynucleotide.

20. The method of embodiment 19, wherein transformed plant or transformed plant cell is produced by transforming at least one plant cell with an expression cassette comprising the first nucleic acid construct and the second nucleic acid construct.

21. The method of embodiment 19, wherein the transformed plant or transformed plant cell is produced by transforming at least one plant cell either simultaneously or sequentially with a first expression cassette comprising the first nucleic acid construct and a second expression cassette comprising the second nucleic acid construct.

22. The method of any one of embodiments 19-21, further comprising regenerating the transformed plant cell into a transformed plant.

23. The method of any one of embodiments 1-19 and 22, wherein the transformed plant is a progeny plant or the transformed plant cell is a cell of the progeny plant, wherein the progeny plant is produced by crossing a first plant with a second plant, the first plant comprising the first nucleic acid construct and the second plant comprising the second nucleic acid construct, and wherein the progeny plant or cell thereof comprises the first nucleic acid construct and the second nucleic acid construct.

24. The method of any one of embodiments 1-23, wherein the first promoter and the second promoter are the same or different promoters.

25. The method of any one of embodiments 1-24, wherein at least one of the first and second promoters is a constitutive promoter.

26. The method of any one of embodiments 1-25, wherein at least one of the first and second promoters is a strong constitutive promoter.

27. The method of any one of embodiments 1-26, wherein the first promoter is the double CaMV 35S promoter.

28. The method of any one of embodiments 1-27, wherein the first promoter comprises the nucleic acid sequence set forth in SEQ ID NO: 9.

29. The method of any one of embodiments 1-28, wherein the second promoter is a GapC promoter.

30. The method of any one of embodiments 1-29, wherein the second promoter comprises the nucleic acid sequence set forth in SEQ ID NO: 12.

31. The method of any one of embodiments 1-30, wherein the transformed plant or transformed plant cell is stably transformed with the first nucleic acid construct, the second nucleic acid construct, or both the first nucleic acid construct, the second nucleic acid construct.

32. The method of any one of embodiments 19-21 and 24-30, wherein the transformed plant or transformed plant cell is transiently transformed with the first nucleic acid construct, the second nucleic acid construct, or both the first nucleic acid construct, the second nucleic acid construct.

33. The method of any one of embodiments 1-32, further comprising growing the transformed plant or transformed plant cell under conditions favorable for the production of asialo-rhuEPO, whereby the transformed plant, plant part, plant cell, or seed thereof or the transformed plant cell produces a high level of asialo-rhuEPO.

34. The method of embodiment of 33, wherein the high level of asialo-rhuEPO is at least about 50, 75, 100, 125, 150, 175, 200, 225, or 250 ng asialo-rhuEPO per mg of total soluble protein.

35. The method of any one of embodiments 1-34, wherein the transformed plant or transformed plant cell is a dicot.

36. The method of embodiment 35, wherein the dicot is selected from the group consisting of tobacco, soybean, *Brassica* spp., cotton, tomato, potato, sweet potato, sunflower, safflower, and peanut.

37. The method of embodiment 35 or 36, wherein the dicot is *Nicotiana tabacum*.

38. The method of any one of embodiments 1-34, wherein the transformed plant or transformed plant cell is a monocot.

39. The method of embodiment 38, wherein the monocot is selected from the group consisting of wheat, rice, maize, barley, sorghum, banana, duckweed, and sugarcane.

40. The method of any one of embodiments 1-39, further comprising purifying the asialo-rhuEPO from the transformed plant, the transformed plant cell, or a part, cell, or seed of the transformed plant.

41. The method of embodiment 40, wherein purifying the asialo-rhuEPO comprises at least one of the following steps: making an aqueous extract of leaves comprising asialo-rhuEPO, removing chlorophyll and/or RuBisCO protein from the aqueous extract, binding the asialo-rhuEPO in the aqueous extract to an immune affinity column, and eluting the bound asialo-rhuEPO from the immune affinity column.

42. The method of embodiment 40 or 41, wherein purifying the asialo-rhuEPO comprises the steps of making an aqueous extract of leaves comprising asialo-rhuEPO, removing chlorophyll and/or RuBisCO protein from the aqueous extract, binding the asialo-rhuEPO in the aqueous extract to an immune affinity column, and eluting the bound asialo-rhuEPO from the immune affinity column.

43. Asialo-rhuEPO produced by the method according to any one of embodiments 1-42.

44. A method for producing a plant or plant cell suitable for the production of asialo-rhuEPO comprising introducing into a plant or plant cell a first nucleic acid construct comprising a first promoter that drives expression in a plant cell operably linked to a first polynucleotide encoding a human EPO fusion protein and a second nucleic acid construct comprising a second promoter that drives expression in a plant cell operably linked to a second polynucleotide encoding a mammalian β1,4-galactosyltransferase.

45. The method of embodiment 44, wherein the human EPO fusion protein comprises a human EPO domain and further comprises at least one operably linked additional domain selected from the group consisting of a protease cleavage domain, a tag domain, and an ER retention signal domain.

46. The method of embodiment 44 or 45, wherein the human EPO fusion protein further comprises in operable linkage a protease cleavage domain, a tag domain, and an ER retention signal domain.

47. The method of any one of embodiments 44-46, wherein the human EPO fusion protein comprises in operable linkage and in an N-terminal to C-terminal direction, a human EPO domain, a protease cleavage domain, a tag domain, and an ER retention signal domain.

48. The method of any one of embodiments 45-47, wherein the protease cleavage domain is the tobacco etch virus (TEV) cleavage domain.

49. The method of embodiment 48, wherein the TEV cleavage domain comprises the amino acid sequence set forth in SEQ ID NO: 5.

50. The method of any one of embodiments 45-47, wherein the tag domain is a StrepII tag domain.

51. The method of embodiment 50, wherein the StrepII tag domain comprises the amino acid sequence set forth in SEQ ID NO: 6.

52. The method of any one of embodiments 45-51, wherein the ER retention signal domain comprises the amino acid sequence set forth in SEQ ID NO: 7.

53. The method of any one of embodiments 45-51, wherein the ER retention signal domain comprises the amino acid sequence set forth in SEQ ID NO: 8.

54. The method of any one of embodiments 45-53, wherein the human EPO domain comprises an amino acid sequence selected from the group consisting of:
(a) the amino acid sequence set forth in SEQ ID NO: 4; and
(b) the amino acid sequence encoded by the nucleic acid sequence set forth in SEQ ID NO: 3.

55. The method of any one of embodiments 45-54, wherein the human EPO domain is encoded by a nucleic acid sequence selected from the group consisting of:
(a) the nucleic acid sequence set forth in SEQ ID NO: 3; and (b) a nucleic acid sequence encoding the amino acid sequence set forth in SEQ ID NO: 4.

56. The method of any one of embodiments 44-55, wherein the human EPO fusion protein comprises an amino acid sequence selected from the group consisting of:

(a) the amino acid sequence set forth in SEQ ID NO: 2; and (b) the amino acid sequence encoded by the nucleic acid sequence set forth in SEQ ID NO: 1.

57. The method of any one of embodiments 44-56, wherein the first polynucleotide comprises a nucleic acid sequence selected from the group consisting of:

(a) the nucleic acid sequence set forth in SEQ ID NO: 1; and (b) a nucleic acid sequence encoding the amino acid sequence set forth in SEQ ID NO: 2.

58. The method of any one of embodiments 44-57, wherein the β1,4-galactosyltransferase is a mammalian β1,4-galactosyltransferase.

59. The method of any one of embodiments 44-58, wherein the β1,4-galactosyltransferase is a human β1,4-galactosyltransferase.

60. The method of any one of embodiments 44-59, wherein the β1,4-galactosyltransferase comprises an amino acid sequence selected from the group consisting of:

(a) the amino acid sequence set forth in SEQ ID NO: 11; and (b) the amino acid sequence encoded by the nucleic acid sequence set forth in SEQ ID NO: 10.

61. The method of any one of embodiments 44-60, wherein the second polynucleotide comprises a nucleic acid sequence selected from the group consisting of:

(a) the nucleic acid sequence set forth in SEQ ID NO: 10; and (b) a nucleic acid sequence encoding the amino acid sequence set forth in SEQ ID NO: 11.

62. The method of any one of embodiments 44-61, wherein the first promoter and the second promoter are the same or different promoters.

63. The method of any one of embodiments 44-62, wherein at least one of the first and second promoters is a constitutive promoter.

64. The method of any one of embodiments 44-63, wherein at least one of the first and second promoters is a strong constitutive promoter.

65. The method of any one of embodiments 44-64, wherein the first promoter is the double CaMV 35S promoter.

66. The method of any one of embodiments 44-65, wherein the first promoter comprises the nucleic acid sequence set forth in SEQ ID NO: 9.

67. The method of any one of embodiments 44-66, wherein the second promoter is a GapC promoter.

68. The method of any one of embodiments 44-67, wherein the second promoter comprises the nucleic acid sequence set forth in SEQ ID NO: 12.

69. The method of any one of embodiments 44-68, wherein the transformed plant or part thereof, or the transformed plant cell, produces a high level of asialo-rhuEPO when grown under conditions favorable for the production of asialo-rhuEPO.

70. The method of embodiment of 69, wherein the high level of asialo-rhuEPO is at least about 50, 75, 100, 125, 150, 175, 200, 225, or 250 ng asialo-rhuEPO per mg of total soluble protein.

71. The method of any one of embodiments 44-70, wherein the transformed plant or transformed plant cell is a dicot.

72. The method of embodiment 71, wherein the dicot is selected from the group consisting of tobacco, soybean, *Brassica* spp., cotton, tomato, potato, sweet potato, sunflower, safflower, and peanut.

73. The method of embodiment 71 or 72, wherein the dicot is *Nicotiana tabacum.*

74. The method of any one of embodiments 44-70, wherein the transformed plant or transformed plant cell is a monocot.

75. The method of embodiment 74, wherein the monocot is selected from the group consisting of wheat, rice, maize, barley, sorghum, banana, duckweed, and sugar-cane.

76. The method of any one of embodiments 44-75, wherein introducing into the plant or the plant cell at least one of the first nucleic acid construct and the second nucleic acid construct comprises a member selected from the group consisting of stable transformation, transient transformation, and sexual reproduction.

77. A transformed plant or transformed plant cell comprising stably incorporated in its genome a first nucleic acid construct comprising a first promoter that drives expression in a plant cell operably linked to a first polynucleotide encoding a human EPO fusion protein and a second nucleic acid construct comprising a second promoter that drives expression in a plant cell operably linked to a second polynucleotide encoding a mammalian β1,4-galactosyltransferase.

78. The transformed plant or transformed plant cell of embodiment 77, wherein the human EPO fusion protein comprises a human EPO domain and further comprises at least one operably linked additional domain selected from the group consisting of a protease cleavage domain, a tag domain, and an ER retention signal domain.

79. The transformed plant or transformed plant cell of embodiment 77 or 78, wherein the human EPO fusion protein further comprises in operable linkage a protease cleavage domain, a tag domain, and an ER retention signal domain.

80. The transformed plant or transformed plant cell of any one of embodiments 77-79, wherein the human EPO fusion protein comprises in operable linkage and in an N-terminal to C-terminal direction, a human EPO domain, a protease cleavage domain, a tag domain, and an ER retention signal domain.

81. The transformed plant or transformed plant cell of any one of embodiments 78-80, wherein the protease cleavage domain is the tobacco etch virus (TEV) cleavage domain.

82. The transformed plant or transformed plant cell of embodiment 81, wherein the TEV cleavage domain comprises the amino acid sequence set forth in SEQ ID NO: 5.

83. The transformed plant or transformed plant cell of any one of embodiments 78-82, wherein the tag domain is a StrepII tag domain.

84. The transformed plant or transformed plant cell of embodiment 83, wherein the StrepII tag domain comprises the amino acid sequence set forth in SEQ ID NO: 6.

85. The transformed plant or transformed plant cell of any one of embodiments 78-84, wherein the ER retention signal domain comprises the amino acid sequence set forth in SEQ ID NO: 7.

86. The transformed plant or transformed plant cell of any one of embodiments 78-84, wherein the ER retention signal domain comprises the amino acid sequence set forth in SEQ ID NO: 8.

87. The transformed plant or transformed plant cell of any one of embodiments 78-86, wherein the human EPO domain comprises an amino acid sequence selected from the group consisting of:
   (a) the amino acid sequence set forth in SEQ ID NO: 4; and
   (b) the amino acid sequence encoded by the nucleic acid sequence set forth in SEQ ID NO: 3.

88. The transformed plant or transformed plant cell of any one of embodiments 78-87, wherein the human EPO domain is encoded by a nucleic acid sequence selected from the group consisting of:
   (a) the nucleic acid sequence set forth in SEQ ID NO: 3; and
   (b) a nucleic acid sequence encoding the amino acid sequence set forth in SEQ ID NO: 4.

89. The transformed plant or transformed plant cell of any one of embodiments 77-88, wherein the human EPO fusion protein comprises an amino acid sequence selected from the group consisting of:
   (a) the amino acid sequence set forth in SEQ ID NO: 2; and
   (b) the amino acid sequence encoded by the nucleic acid sequence set forth in SEQ ID NO: 1.

90. The transformed plant or transformed plant cell of any one of embodiments 77-89, wherein the first polynucleotide comprises a nucleic acid sequence selected from the group consisting of:
   (a) the nucleic acid sequence set forth in SEQ ID NO: 1; and
   (b) a nucleic acid sequence encoding the amino acid sequence set forth in SEQ ID NO: 2.

91. The transformed plant or transformed plant cell of any one of embodiments 77-90, wherein the β1,4-galactosyltransferase is a mammalian β1,4-galactosyltransferase.

92. The transformed plant or transformed plant cell of any one of embodiments 77-91, wherein the β1,4-galactosyltransferase is a human β1,4-galactosyltransferase.

93. The transformed plant or transformed plant cell of any one of embodiments 77-92, wherein the β1,4-galactosyltransferase comprises an amino acid sequence selected from the group consisting of:
   (a) the amino acid sequence set forth in SEQ ID NO: 11; and
   (b) the amino acid sequence encoded by the nucleic acid sequence set forth in SEQ ID NO: 10.

94. The transformed plant or transformed plant cell of any one of embodiments 77-93, wherein the second polynucleotide comprises a nucleic acid sequence selected from the group consisting of:
   (a) the nucleic acid sequence set forth in SEQ ID NO: 10; and
   (b) a nucleic acid sequence encoding the amino acid sequence set forth in SEQ ID NO: 11.

95. The transformed plant or transformed plant cell of any one of embodiments 77-94, wherein the first promoter and the second promoter are the same or different promoters.

96. The transformed plant or transformed plant cell of any one of embodiments 77-95, wherein at least one of the first and second promoters is a constitutive promoter.

97. The method of any one of embodiments 77-96, wherein at least one of the first and second promoters is a strong constitutive promoter.

98. The transformed plant or transformed plant cell of any one of embodiments 77-97, wherein the first promoter is the double CaMV 35S promoter.

99. The transformed plant or transformed plant cell of any one of embodiments 77-98, wherein the first promoter comprises the nucleic acid sequence set forth in SEQ ID NO: 9.

100. The transformed plant or transformed plant cell of any one of embodiments 77-99, wherein the second promoter is a GapC promoter.

101. The transformed plant or transformed plant cell of any one of embodiments 77-100, wherein the second promoter comprises the nucleic acid sequence set forth in SEQ ID NO: 12.

102. The transformed plant or transformed plant cell of any one of embodiments 77-101, wherein the transformed plant or part thereof, or the transformed plant cell, produces a high level of asialo-rhuEPO when grown under conditions favorable for the production of asialo-rhuEPO.

103. The transformed plant or transformed plant cell of embodiment of 102, wherein the high level of asialo-rhuEPO is at least about 50, 75, 100, 125, 150, 175, 200, 225, or 250 ng asialo-rhuEPO per mg of total soluble protein.

104. The transformed plant or transformed plant cell of any one of embodiments 77-103, wherein the transformed plant or transformed plant cell is a dicot.

105. The transformed plant or transformed plant cell of embodiment 104, wherein the dicot is selected from the group consisting of tobacco, soybean, *Brassica* spp., cotton, tomato, potato, sweet potato, sunflower, safflower, and peanut.

106. The transformed plant or transformed plant cell of embodiment 104 or 105, wherein the dicot is *Nicotiana tabacum*.

107. The transformed plant or transformed plant cell of any one of embodiments 77-103, wherein the transformed plant or transformed plant cell is a monocot.

108. The transformed plant or transformed plant cell of embodiment 107, wherein the monocot is selected from the group consisting of wheat, rice, maize, barley, sorghum, banana, duckweed, and sugarcane.

109. The transformed plant or transformed plant cell of any one of embodiments 77-108, wherein the plant is a seed and the transformed plant cell is a seed cell.

110. A method for purifying asialo-rhuEPO from plant tissue comprising:
   (a) making an aqueous extract of plant tissue, wherein the plant tissue comprises asialo-rhuEPO;
   (b) removing chlorophyll and/or RuBisCO protein from the aqueous extract;
   (c) binding the asialo-rhuEPO in the aqueous extract to an immune affinity column; and
   (d) eluting the bound asialo-rhuEPO from the immune affinity column.

111. The method of embodiment 110, wherein the plant tissue comprises leaves.

112. The method of embodiment 111, wherein the leaves are harvested from a transgenic tobacco plant.

113. The method of embodiment 113, wherein the transgenic tobacco plant is a transformed plant according to embodiment 105 or 106.

114. The method of embodiment 112 or 113, wherein the transgenic tobacco plant was grown under conditions favorable for the production of asialo-rhuEPO before the leaves were harvested.

115. A method of treatment comprising administering to a human individual an effective amount of plant-produced asialo-rhuEPO.

116. The method of embodiment 115, wherein the asialo-rhuEPO is produced by the method according to any one of embodiments 1-42.

117. The method of embodiment 115 or 116, wherein an effective amount of asialo-rhuEPO is an amount of the asialo-rhuEPO that has been determined to provide a tissue protective effect to at least one human individual.

118. The method of any one of embodiments 115-117, wherein the asialo-rhuEPO is purified by the method according to any one of embodiments 110-114.

The invention is further described below including additional embodiments of methods for producing asialo-rhuEPO and for purifying asialo-rhuEPO from plant tissues, plant expressions systems, transformed plants, plant parts, plant cells, and seeds as well as expression cassettes and nucleic acid constructs useful in the methods and transformed plants and transformed plant cells disclosed herein.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotides of the present invention can be provided in expression cassettes for expression in the plant and/or plant cells of interest. The expression cassette will include 5' and 3' regulatory sequences operably linked to the gene of interest to be expressed. "Operably linked", "in operable linkage", and similar terms are each intended to mean a functional linkage between two or more elements. For example, an operable linkage between one or more genetic regulatory elements and a gene of interest is functional link between the gene of interest and the one or more genetic regulatory elements that allows for expression of the gene of interest. If desired and/or necessary to maintain the desired function of, for example, a fusion protein encoded by the operably linked elements, a linker sequence can be added between any of the two or more elements that are joined. It is recognized that suitable linker sequences are known in the art and can be used in the methods disclosed herein. Operably linked elements may be contiguous or non-contiguous.

When used to refer to the joining of two protein coding regions, by "operably linked", "in operable linkage", and similar terms are each are intended to mean that the coding regions are in the same reading frame. When used to refer to the joining of two or more amino acid sequences or protein domains for a fusion protein of the present invention "operably linked", "in operable linkage", and similar terms are each intended to mean that the amino acid sequences are joined to produce a single amino acid sequence. If desired and/or necessary to maintain the desired function of the fusion protein and/or at least one of the domains therein, a linker amino acid sequences can be added between any of the two or more amino acid sequences or protein domains that are joined. It is recognized that suitable linker amino acid sequences are known in the art and can be used in the methods disclosed herein. Operably linked amino acid sequences or protein domains may be contiguous or non-contiguous.

The expression cassette may additionally contain at least one additional gene to be co-transformed into the plant. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), polynucleotide to be expressed, and a transcriptional and translational termination region (i.e., termination region) functional in plants or other organism or host cell. The regulatory regions (i.e., promoters, transcriptional regulatory regions, and translational termination regions) and/or the polynucleotide to be expressed may be native/analogous to the host cell or to each other. Alternatively, any of the regulatory regions and/or the polynucleotide to be expressed may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. A preferred termination region is the terminator from the tobacco GapC gene, which comprises the nucleic acid sequence set forth in SEQ ID NO: 13.

Where appropriate, the genes of interest may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a plant host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS* USA 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Virology 154:9-20), and human immuno-globulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubsti-tutions, e.g., transitions and transversions, may be involved.

The expression cassette can also comprise a selectable marker gene for the selection of transformed cells. Select-able marker genes are utilized for the selection of trans-formed cells or tissues. Marker genes include genes encod-ing antibiotic resistance, such as those encoding neomycin phosphotransferase II (NEO) and hygromycin phospho-transferase (HPT), as well as genes conferring resistance to herbicidal compounds, such as glufosinate ammonium, bro-moxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng.* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol.* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *PNAS* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *PNAS* 86:5400-5404; Fuerst et al. (1989) *PNAS* 86:2549-2553; Deuschle et al. (1990)

*Science* 248:480-483; Gossen (1993) Ph.D. Thesis, Univer-sity of Heidelberg; Reines et al. (1993) *PNAS* 90:1917-1921; Labow et al. (1990) *Mol. Cell. Biol.* 10:3343-3356; Zam-bretti et al. (1992) *PNAS* 89:3952-3956; Baim et al. (1991) *PNAS* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimi-crob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *PNAS* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Ber-lin); Gill et al. (1988) *Nature* 334:721-724. Such disclosures are herein incorporated by reference.

The above list of selectable marker genes is not meant to be limiting. Any selectable marker gene can be used in the present invention.

Numerous plant transformation vectors and methods for transforming plants are available. See, for example, An, G. et al. (1986) *Plant Pysiol.,* 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene* 118:255-260; Christou, et al. (1992) *Trends. Biotech-nol.* 10:239-246; D'Halluin, et al. (1992) *Bio/Technol.* 10:309-314; Dhir, et al. (1992) *Plant Physiol.* 99:81-88; Casas et al. (1993) *PNAS* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; Guo Chin Sci. Bull. 38:2072-2078; Asano, et al. (1994) Plant Cell Rep. 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technol-ogy* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide, nucleic acid construct, or expression cas-sette into a plant. By "introducing" is intended presenting to the plant the polynucleotide, nucleic acid construct, or expression cassette in such a manner that the construct gains access to the interior of a cell of the plant. The methods of the invention do not depend on a particular method for introducing a polynucleotide, nucleic acid construct, or expression cassette to a plant, only that the polynucleotide, nucleic acid construct, or expression cassette gains access to the interior of at least one cell of the plant. Methods for introducing nucleic acid molecules into plants are known in the art including, but not limited to, stable transformation methods, transient transformation methods, and virus-me-diated methods.

By "stable transformation" is intended that the polynucle-otide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for the delivery foreign DNA or other foreign nucleic acids involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.* 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) PNAS 83:5602-5606, *Agrobacterium*-mediated transformation as described by Townsend et al., U.S. Pat. No. 5,563,055, Zhao et al., U.S. Pat. No. 5,981,840, Yukou et al., WO 94/000977, and Hideaki et al., WO 95/06722, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *PNAS* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *PNAS* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. It is recognized that the a protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

In specific embodiments, the nucleic acid molecules and polynucleotide constructs of the present invention can be provided to a plant using a variety of transient transformation methods. Such transient transformation methods include, but are not limited to, the introduction of the sequence or variants and fragments thereof directly into the plant or the introduction of a transcript into the plant. Such methods include, for example, microinjection, electroporation, or particle bombardment. See, for example, Crossway et al. (1986) *Mol Gen. Genet.* 202:179-185; Nomura et al. (1986) *Plant Sci.* 44:53-58; Hepler et al. (1994) *PNAS* 91: 2176-2180 and Hush et al. (1994) *The Journal of Cell Science* 107:775-784, Sheen, J. 2002. A transient expression assay using maize mesophyll protoplasts. http://genetics.mgh.harvard.edu/sheenweb/, Anderson et al., U.S. Pat. No. 7,645,919 B2, all of which are herein incorporated by reference. Alternatively, the polynucleotide can be transiently transformed into the plant using techniques known in the art.

The nucleic acid molecules and polynucleotide constructs of the present invention can be used for transformation of any plant species, including, but not limited to, monocots and dicots. Examples of plant species of interest include, but are not limited to, *Arabidopsis thaliana*, peppers (*Capsicum* spp; e.g., *Capsicum annuum, C. baccatum, C. chinense, C. frutescens, C. pubescens*, and the like), tomatoes (*Lycopersicon esculentum*), tobacco (*Nicotiana tabacum*), eggplant (*Solanum melongena*), *petunia* (*Petunia* spp., e.g., *Petunia* x *hybrida* or *Petunia hybrida*), corn or maize (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), green millet (*Setaria viridis*), finger millet (*Eleusine coracana*)), sunflower (*Helianthus annuus*), safflower (Carthamus tinctorius), wheat (*Triticum aestivum*), soybean (*Glycine max*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus* casica), guava (*Psidium guajava*), mango (*Mangifera indica*), olive (*Olea europaea*), papaya (*Carica papaya*), cashew (*Anacardium occidentale*), macadamia (Macadamia *integrifolia*), almond (*Prunus* amygdalus), sugar beets (*Beta vulgaris*), sugarcane (*Saccharum* spp.), switchgrass (*Panicum virgatum*), algae (e.g., *Chlamydomonas reinhardtii, Botryococcus braunii, Chlorella* spp., *Dunaliella tertiolecta*, Gracilaria spp.), oats, barley, vegetables, ornamentals, and conifers.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruits, roots, root tips, anthers, and the like. Progeny, variants, and mutants of the regenerated plants are also included within the scope of the invention, provided that these parts comprise the introduced polynucleotides.

The following examples, including those found in the Appendix, are offered by way of illustration and not by way of limitation.

EXAMPLE

Development of a Plant Expression System for the High-Level Production of Cytoprotective Asialo-rhuEPO and its Purification from Plant Tissues The present example describes an embodiment of the invention. In particular, this example describes a method of using plant expression system to highly express a recombinant human erythropoietin (EPO) derivative-asialoerythropoietin (asialo-rhuEPO), and a method for the purification of this protein from leaf tissues. The expression method includes the steps of providing a doubled CaMV 35S (35S$^2$) promoter, a sequence encoding for human EPO (target protein) and a sequence for the addition of a TEV protease cleavage peptide, StrepII and KDEL tags fused to the C-terminus of EPO; providing a glyceraldehydes-3-phosphate dehydrogease gene (GapC) promoter and a sequence encoding for a N-glycosylation modification enzyme human β1,4-galactosyltransferase; constructing an expression vector containing a gene of target protein, another gene for N-glycosylation modification enzyme, and a selective marker gene; expressing the expression vector in plants. The purification method includes the steps of removing chlorophylls and RuBisCO protein; binding asialo-rhuEPO to immune affinity column; and removing BSA protein from eluted asialo-rhuEPO solution.

Erythropoietin (EPO) is a glycoprotein hormone, which displays both hematopoietic and tissue protective functions by binding to two distinct receptors. Recombinant human EPO (rhuEPO) is widely used for the treatment of anemia in patients with renal failure, but its use for tissue protection is limited because of potentially harmful increase in the red blood cell mass when higher doses of rhuEPO are used for tissue protection. Recent studies have shown that asialo-erythropoietin (asialo-rhuEPO), a desialylated form of EPO, lacks hematopoietic activity, but retains cytoprotective function. Currently, a small amount of asialo-rhuEPO can be produced by enzymatic or chemical desialylation of rhuEPO. The prohibitive cost of rhuEPO, however, is a major limitation of the above methods for its production. In this example, we disclose that asialo-rhuEPO was highly expressed in *Nicotiana tabacum* plants by co-expressing human β1,4-galactosyltransferase gene (GaiT) with the human EPO gene (EPO) fused with StrepII and KDEL tags and developed a method for the purification of asialo-rhuEPO from leaf tissues. Enzyme-linked immunosorbent assay (ELISA) showed that asialo-rhuEPO accumulated approximately 230 ng/mg TSP in highly expressed transgenic tobacco plants. Western blot analysis of crude extracts and immunoaffinity purified asialo-rhuEPO showed presence of two major immunoreactive bands. Peptide mapping of two major protein bands of sizes 30 kD and 28 kD showed that both bands are asialo-rhuEPO, but different glycoforms. Immunoaffinity purified asialo-rhuEPO bound to *Erythrina cristagalli* lectin-agarose column, indicating that its N-glycan chains bear terminal β1,4-galactose residues and that the co-expressed GalT is functionally active. In the in vitro receptor binding assay, asialo-rhuEPO bound to its primary receptor (EPOR) with similar affinity as Chinese hamster ovary (CHO) cells-produced rhuEPO, implying that the plant-produced asialo-rhuEPO is properly folded. The results of the in vitro cytoprotection assay demonstrated that plant-produced asialo-rhuEPO provides a better cytoprotective effect than mammalian cell-produced rhuEPO. The invention described here provides a straightforward and a potentially cheaper way to produce cytoprotective asialo-rhuEPO for research and therapeutic purposes.

The N-glycosylation pathway was engineered in tobacco plants to produce asialo-rhuEPO. The present inventors took the distinct advantage of lack of sialylation capacity in plant expression system and engineered the N-glycosylation pathway to produce asialo-rhuEPO. In previous study (See, Appendix), the present inventors disclosed that tobacco plants, which were modified to express a genetic cassette CEJ120 containing human GalT and EPO fused with an ER-retention signal peptide KDEL, accumulated asialo-rhuEPO (Kittur et al., 2012). Based on those initial results, the inventors further improved production efficiency about 50-fold using a new genetic cassette A56 and developed a purification system to isolate asialo-rhuEPO from transgenic tobacco leaves as described below.

Materials and Methods

Plant Materials

Tobacco (*Nicotiana tabacum* L., cultivar "K326") was used in this invention to generate transgenic plants. Sterilized seedlings for transformation were prepared as described previously (Musa et al. 2009). Transgenic plants were grown under greenhouse conditions for transgene analysis and protein isolation.

Construction of the Expression Vector A56 and *Agrobacterium*-Mediated Transformation A binary vector A56 containing two different promoters driving human EPO and GalT was created and used to transform tobacco plants. A56 was created as follows. First, EPO cDNA sequence was synthesized by Eurofins MWG Operon with adding a cutting site for SpeI at 5' end and a 66 bp sequence at 3'. This 66 bp 3' region codes for a TEV protease cutting site ENLYFQG, two fusion tags StrepII and KDEL, and a SacI cutting site. Addition of TEV protease cutting site was for removing fusion tags in case if these tags have to be removed for a fully functional asialo-rhuEPO. StrepII was used to aid in the purification of protein while KDEL was used to target protein to the ER. Doubled CaMV 35S ($35S^2$) promoter was created by PCR amplification by adding HindIII cutting site at 5' end and SpeI cutting site at the 3' end based on information from an expression vector pKYLX71:$35S^2$ (Maiti et al. 1993). It was sub-cloned into pCR®2.1 Vector purchased from Invitrogen to create a new plasmid DNA CEJ887. The synthetic EPO fragment was isolated by restriction enzymes SpeI and EcoRI and sub-cloned into the vector CEJ887 at SpeI and EcoRI sites. The resultant plasmid DNA CEJ890 contains a CaMV $35S^2$ promoter driving EPO. Then a $35S^2$ promoter driving EPO fragment was isolated from CEJ890 by HindIII and SacI and sub-cloned into HindIII and SacI sites of an expression vector pBI121 (Accession No. AF485783). The pBI121 vector after digestion contains a nopaline synthase gene (nos) promoter driving a neomycin phosphotransferase gene (nptII) and nos terminator and additional nos terminator. This new plasmid DNA CEJ896 contains a nos promoter driving nptII with a nos terminator and a CaMV $35S^2$ promoter driving EPO with a nos terminator. A GalT cassette containing GapC promoter driving GalT with GapC terminator was isolated from plasmid DNA CEJ120 and cloned into CEJ896. The resultant construct CEJ902 containing GapC, $35S^2$ and nos promoters driving GalT, EPO and nptII, respectively, was introduced into *Agrobacterium tumefaciens* strain LBA4404 using freeze-thaw method (Holster et al. 1978) and re-named as A56 (FIG. 1).

Confirmation of the Presence of GalT, EPO and nptII in Transgenic Plants

To confirm the presence of the EPO and GalT in kanamycin resistant plants, PCR amplification was performed using primers EPOPF (5'-TAATTCTAGAATGCACCATCAT-CATCATCATGGGGTGCACGA-3') (SEQ ID NO: 14)/ EPOPR (5'-AATTGAGCTCCTAGAGCT-CATCTTTTCTGTCCCCTGTCCTGC-3') (SEQ ID NO: 15) for EPO (Musa et al. 2009) and GalTF7 (forward: 5'-CTGGCTATATTATTTGCACCC-3') (SEQ ID NO: 16)/ GalTR7 3' (reverse: 5'-ATTGTCTCCTTTGTGTGTGC-3') (SEQ ID NO: 17) for GalT. NptIIPF (5'-AAGATGGAT-TGCACGCAGGTTC) (SEQ ID NO: 18)/NptIIPR (5'-ACGGGTAGCCAACGCTATGTC-3') (SEQ ID NO: 19) primers were used to detect the presence of nptII. Total genomic DNA isolation and PCR conditions for EPO, GalT and nptII analyses were as reported previously (Musa et al. 2009).

Quantification of EPO Transcripts in Transgenic Plants by Quantitative Real Time PCR (qRT-PCR)

QRT-PCR was performed on selected transgenic plants to detect and quantify EPO transcripts. Qiagen RNeasy® Plant Mini kit (Qiagen, Valencia, CA, USA) was used to isolate RNA. Isolated RNA was treated with DNase I to remove any DNA contamination. Equal amounts of RNA isolated from each sample were used to synthesize first-strand cDNA using MultiScribe Reverse Transcriptase and random primers (Applied Biosystems, Carlsbad, CA, USA). For primer design, SYBR green PCR Master Mixture (Applied Biosystems) and $\Delta\Delta$Ct calculation, we used methods as described previously (Hung et al., 2010). The QuantumRNA™ 18S Internal Standard (Ambion, Austin, TX, USA) was used as an endogenous control. Each sample was assayed in triplicates.

Protein Extraction and Purification

For protein extraction, leaf tissue (200 g) was weighed and ground into a fine powder in liquid nitrogen. The powder was then extracted with phosphate buffered saline (PBS), pH 7.3 containing 0.1% Tween-20, 1 mM EDTA, 100 mM ascorbic acid, 2% polyvinylpolyprrolidone and plant protease inhibitor cocktail (Sigma, Saint Louis, MO, USA). Extraction buffer was added to the leaf tissue in the ratio of 3 ml buffer:1 g of leaf tissue. Insoluble plant debris was removed by passing the extract through double layers of miracloth (EMD Biosciences, San Diego, CA, USA). Fine particulates were removed by two rounds of centrifugation at 20,000 g for 15 min. The pH of the extract was then adjusted to 5.0 with 2 M Tris-HCl (pH 9.0). To remove chlorophyll, solid ammonium sulfate (80.84 g) was added to a final concentration of 25%. Following incubation on ice for 2 h, precipitated chlorophyll/proteins was removed by centrifugation at 20,000 g for 15 min. The supernatant was carefully decanted and then to it was added solid ammonium sulfate (156 g) to a final concentration of 65%. The suspension was stirred gently using a magnetic stirrer overnight at 4° C. Protein precipitate (containing asialo-rhuEPO) was collected by centrifugation at 20,000 g for 15 min. Asialo-rhuEPO was further purified using immunoaffinity chromatography as described below.

Immunoaffinity Chromatography (IAC)

The antibody column for IAC was prepared by coupling rabbit polyclonal anti-EPO antibody (E2531, Sigma Chemical Company, MO, USA) to agarose resin using AminoLink Plus immobilization kit (Thermo Scientific, Rockford, IL, USA). Briefly, 10 mg of anti-EPO antibody was dissolved in 0.1 M citrate-carbonate buffer, pH 10.0 (coupling buffer). BSA was added to antibody solution to a final concentration of 0.1% to stabilize the antibody. For coupling, the activated resin (10 ml) was first spun to remove storage buffer, and followed by two washes (10 ml each) of coupling buffer to equilibrate the resin. Coupling was conducted at 4° C. (overnight) on an end-to-end rocking shaker. Following incubation, the resin was washed with 0.1 M PBS, reduced with sodium cyanoborohydride and the remaining binding sites were blocked with quenching buffer (1M Tris-HCl). Following immobilization, the antibody coupled resin was stored at 4° C. in PBST containing 0.05% sodium azide.

For asialo-rhuEPO purification, the protein pellet obtained by adding 65% ammonium sulfate as described in last section (i.e., "Protein extraction and purification") was dissolved in 30 ml of PBS and mixed with 30 ml of PBST containing 2.7% BSA. The protein mixture was added to 10 ml of anti-EPO antibody coupled resin, which had been previously equilibrated with PBST. The mixture was kept on an end-to-end rocking shaker overnight at 4° C. for binding. Following binding, the resin was packed in a 15 ml glass column. Unbound proteins were removed by washing the resin with 5 column volumes (CV) (50 ml) of PBST. Bound asialo-rhuEPO was eluted with 0.1 M glycine-HCl buffer, pH 2.5. Ten fractions of 4.5 ml each were collected and neutralized immediately by adding 0.5 ml of 2 M Tris-HCl buffer, pH 9.0. The concentrations of asialo-rhuEPO were determined by Bradford and sandwich ELISA, respectively as described below. Peak fractions were pooled and concentrated using 10 kD cut-off 15 ml Centripep® centrifugal filter device (EMD Millipore, Billerica, MA, USA).

Removal of BSA after IAC Chromatography

The IAC fractions contained some residual BSA, whose concentration increased substantially (10 times of the asialo-rhuEPO) upon pooling and concentrating the fractions. To remove BSA, Melon Gel IgG spin purification kit (Thermo Scientific, Rockford, IL, USA) was used. Briefly, 155 µl of concentrated IAC purified asialo-rhuEPO was mixed with 345 µl of Melon-gel buffer. The diluted sample was then incubated with Melon-gel (100 µl) for 10 min at room temperature. Following incubation, the sample was spun at 1000 rpm for 2 min and the flow through was collected. The flow through was further concentrated using a 2 ml 10 kD cut-off Centripep® centrifugal filter device and subjected to SDS-PAGE as described below.

Protein Concentration Determination

Protein concentration was determined as described in Kittur et al. (2012) with Bradford reagent using crystalline bovine serum albumin as a standard (0-1.0 mg/ml concentration range). The microassay format in 96-well flat bottom plates was employed as described by the manufacturer (Bio-Rad, Hercules, CA, USA). After 5 min of incubation of the dye reagent and protein mixture, the absorbance was read at 595 nm on a VersaMax plate reader (Molecular Devices, Sunnyvale, CA, USA).

Quantification of Asialo-rhuEPO by ELISA

To detect and quantify asialo-rhuEPO in transgenic tobacco leaf extracts and various chromatography fractions, a sandwich ELISA protocol developed by Conley et al (2009) was used with some modifications. Briefly, ELISA plates were coated with 2 µg/ml mouse anti-EPO monoclonal antibody (01350, Stem Cell Technologies, Vancouver, BC, Canada) in 0.1 M disodium phosphate buffer (pH 9.2) and incubated overnight at 4° C. The wells were blocked with 2.7% BSA in PBS for 1 h at room temperature. Following blocking, leaf extracts (50 µl) or IAC column fractions (20 µl) were mixed with blocking buffer (PBS containing 2.7% BSA and 0.05% Tween-20) to a final volume of 400 µl, applied onto the plate, and incubated overnight at 4° C. The plate was then incubated with 4 µg/ml rabbit anti-EPO antibody (E2531, Sigma Chemical Company, MO, USA) in blocking buffer for 3 h at room temperature. This was followed by incubation with 1:1000 diluted (in blocking buffer) HRP-conjugated goat anti-rabbit IgG (Jackson Immuno Research, West Grove, PA, USA) for 1 h. The plate was washed four times between incubation steps with PBS containing 0.05% Tween-20. The plate was developed by the addition of 2, 2'-bis (3-ethylbenthiazoline)-6-sulfonic acid substrate and the absorbance at 405 nm was measured using a VersaMax plate reader. A standard curve was generated using CHO cell-produced rhuEPO in the concentration ranges of 0-10 ng/ml. Each sample was assayed in triplicate.

Western Blot Analysis

For western blot analysis, crude plant extracts or purified asialo-rhuEPO were boiled with Laemmli sample buffer (Laemmli, 1970). Proteins were separated on a 12.5% SDS/PAGE gel. Following separation, proteins were transferred onto a PVDF membrane using 10 mM CAPS (pH 11) as transfer buffer. Protein transfer was done at 4° C. overnight. The membrane was blocked with 10% skim milk dissolved in PBST, followed by incubation with mouse anti-EPO monoclonal antibody (0.5 µg/ml) (MAB2871; R&D Systems, Minneapolis, MN, USA) at room temperature for 1 h with gentle shaking. A secondary HRP-conjugated goat anti-mouse IgG antibody (dilution of 1:5000) (Jackson Immuno Research, West Grove, PA, USA) was used to detect primary antibody. The membrane was washed three times with PBS containing 0.1% Tween-20 after each incubation with antibody solution. The luminescent signal was generated after 1 min incubation with SuperSignal® West Pico Chemiluminescent substrate (Thermo Scientific, Rockford, USA) and captured by Kodak Biomax light film (PerkinElmer, Waltham, MA, USA).

SDS-PAGE and LC-MS/MS Analysis

About 7 µg of IAC purified EPO and 4 µg of CHO cell-produced rhuEPO were boiled with Laemmli sample buffer (Laemmli, 1970) and separated on a 12.5% 1.5 mm thick Tris-glycine SDS gel. Electrophoresis was carried out at 200 V for 1 h. Following separation, the gel was fixed in methanol:acetic acid:$H_2O$ (50:10:50) followed by staining with coomassie blue. The gel was destained with a mixture of methanol:acetic acid:$H_2O$ (45:10:45). Protein bands corresponding to major immunoreactive bands on western blot were excised, and were analyzed by LC-MS/MS for protein identification at Duke Proteomic Facility, Duke University, Durham, NC.

Binding of Purified Plant-Produced Asialo-rhuEPO to 1,4-Galactose Specific *Eythrina Cristagalli* (ECA)-Agarose Lectin Column To investigate whether plant-produced asialo-rhuEPO N-glycan chains bear β1,4-linked galactose residues, binding of asialo-rhuEPO to ECA-agarose column was performed. Briefly, purified asialo-rhuEPO (140 ng) was first diluted in 20 mM HEPES-KOH buffer, pH 7.3 containing 5 mM $MgCl_2$ and 100 mM NaCl (column wash buffer, CWB). It then was mixed with 1.0 ml ECA-agarose resin (EY Laboratories, San Mateo, CA, USA), which had been equilibrated with CWB. Binding was conducted at 4° C. overnight on an end-to-end rocking shaker. After binding, the resin was packed in a column. Unbound non-galactosylated rhuEPO was removed by washing with 10 ml CWB. Bound asialo-rhuEPO was eluted with CWB containing 0.2 M lactose. Same amount of asialoagalacto-rhuEPO purified from transgenic tobacco line EPO9 expressing EPO alone (Musa et al. 2009) was used as a negative control. Ten fractions of 1 ml each were collected. ELISA as described above was used to quantify asialo-rhuEPO in the flow through, wash and bound fractions.

In Vitro Receptor-Binding Assay

An indirect ELISA developed by Conley et al. (2009) was used to assess the binding of the plant-produced asialo-rhuEPO fusion protein to hematopoietic receptor EPOR. Briefly, a 96-well plate was coated with mouse anti-EPOR antibody (4 µg/ml) (R&D Systems, Inc, Minneapolis, MN, USA) in disodium phosphate buffer (pH 9.2) and incubated overnight at 4° C. The plate was washed and blocked with 2.7% BSA in PBS for 1 h at room temperature. RhuEPO, purified plant-produced asialoagalacto-rhuEPO and asialo-rhuEPO were serially diluted (0.5-0.0078 nM) in ELISA blocking buffer containing 20 ng/ml EPOR. Following incubation on ice for 15 min, the reaction mixture was applied onto an antibody coated microtiter plate and incubated overnight at 4° C. The remainder of the procedure to detect bound EPO was performed as described for quantitative ELISA. Dissociation constant ($K_d$) was calculated from the non-linear curve fitting of $A_{405\ nm}$ data (ELISA detection signal) using GraphPad Prism version 5. Experiment was repeated once.

In Vitro Cytoprotection Assay

Mouse neuroblastoma cell line (N2A) (American Type Culture Collection) was maintained in Dulbecco's modified Eagle's medium (DMEM) (Thermo Scientific, Rockford, IL, USA) with high glucose, containing 10% FBS and penicillin/streptomycin (100 U/ml and 100 µg/ml, respectively) at 37° C. and 5% $CO_2$. For EPO-mediated cytoprotection assay, N2A cells were seeded at a density of $4.0\times10^4$ in 96-well cell culture plates for lactate dehydrogenase (LDH) assay or at a density of $8.0\times10^5$ in 15 ml T-flask for western blot analysis. They were incubated at 37° C. in 5% $CO_2$ until they reached 70% confluence. Cells were then treated simultaneously with 20 U/ml purified asialo-rhuEPO$^P$ or rhuEPO$^M$ (R&D Systems, Minneapolis, MN, USA) in PBS containing 0.1% BSA and 1 µM staurosporine (STS) directly added to the medium. As a vehicle control, same volume of PBS containing 0.1% BSA was added to the medium. For STS alone treatment, 1 µM STS in PBS containing 0.1% BSA was included in the medium. The number of asialo-rhuEPO$^P$ units was calculated from protein concentration as described by Erbayraktar et al. (2003). After 12 h of treatment, cell injury was assessed with the non-radioactive cytotoxicity assay kit (Roche Applied Science, Indianapolis, IN, USA) according to the manufacturer's protocol. Each test was performed using six replicates and the average of six replicates was used in the final calculations to compute cytotoxicity.

SDS-PAGE and Western Blot Analysis of p-JAK2/JAK2 and Caspase 3

SDS-PAGE was carried out according to method of Laemmli (1970). For analyzing p-JAK2/JAK2 and caspase 3, N2A cell lysates were prepared by extracting untreated and treated cells using 10 mM HEPES buffer (pH 7.5) containing 2 mM MgCl2, 15 mM KCl, 0.1 mM EDTA, 0.1 mM EGTA, PMSF, protease and phosphatase inhibitor cocktails (Kumari et al., 2012). NP-40 was added immediately before centrifugation at 5000×g. The supernatant was used as cytosolic protein fraction for detection of p-JAK2/JAK2 and caspase 3 by western blot analysis. Protein separation and transfer was performed as described previously (Kittur et al., 2012). The membranes were then blocked for 1 h with 5% BSA in TBST. Blots were incubated separately with anti-caspase 3 (Cell Signaling Technology, Danvers, MA, USA), anti-p-JAK2 (Cell Signaling Technology, Danvers, MA, USA), anti-JAK2 (Santa Cruz Biotechnology, Dallas, Texas, USA) and anti-R-actin (Sigma Chemical Company, Saint Louis, MO, USA) antibodies each at a dilution of 1:1000 except anti-JAK2 (1:400). Blots were incubated overnight at 4° C. Following incubation, blots were washed and incubated with 1:1000 diluted HRP-conjugated secondary antibody for 1 h at room temperature. SuperSignal @West Pico Chemiluminescent substrate was used to detect protein bands.

Results

Creation of Transgenic Tobacco Plants for Expressing Asialo-rhuEPO

In order to produce asialo-rhuEPO in tobacco plants, a genetic construct A56 (FIG. 1) that targets EPO to the ER was designed. EPO and GalT were placed under the control of CaMV 35S$^2$ and tobacco GapC promoters, respectively. A56 was stably transferred into tobacco plants using *Agrobacterium*-mediated transformation (Holster et al. 1978). Only one shoot per leaf disc was isolated for shoot elongation and rooting so that each transformant would be from a different transformation event.

Screening of Kanamycin-Resistant Plants for the Presence of EPO and GalT

A total of 12 kanamycin-resistant plants were screened for the presence of EPO and GalT by PCR as described under "Materials and Methods". The presence of nptII was also analyzed. The results showed that all 12 kanamycin-resistant plants from A56 transformation and one transgenic control plant CEJ120-12 expressing EPO under the control of single CaMV 35S had a PCR product of 670 bp (FIG. 2) when they were amplified by NptIIF/NptIIR primers, which means all kanamycin-resistant plants had nptII. With primers EPOPF/EPOPR for EPO, all 13 plants from A56 and CEJ120 had a PCR product of 620 bp (FIG. 2), indicating the presence of EPO. Similarly, all 13 plants showed a PCR product of size 530 bp corresponding to partial GalT confirming the presence of GalT in transgenic plants (FIG. 2). PCR results showed that both EPO and GalT are present in all 12 transgenic plants. These 12 plants were then used to detect asialo-rhuEPO levels by ELISA.

Quantification of Asialo-rhuEPO in Transgenic Tobacco Plants Using ELISA

To determine the production levels of asialo-rhuEPO in transgenic tobacco plants expressing EPO under the control of a CaMV 35S$^2$ promoter and with fusion tags for StrepII and KDEL, a sandwich ELISA was performed on plant extracts. For comparison purpose, the highest expression transgenic tobacco line CEJ120-12 from our previous CEJ120 transformation experiment (Kittur et al. 2012) was included as an expression level control. In expression vector CEJ120, EPO was under the control of a single CaMV 35S promoter with a KDEL fusion tag, but without StrepII tag. The amount of asialo-rhuEPO present in leaf extracts was estimated by comparing the $A_{405\ nm}$ from a known amount of CHO cell-produced rhuEPO. The amount of asialo-rhuEPO was expressed as a percentage of total soluble protein (TSP) in the leaf extracts. As can be seen from FIG. 3, the accumulation levels of asialo-rhuEPO varied greatly among the transgenic lines, which could be due to chromosomal position effects associated with random gene insertion. Among 12 transgenic lines analyzed by ELISA, 4 transgenic lines (A56-2, -5, -11 and -12) had 30- to 50-fold higher asialo-rhuEPO accumulation (171-231 ng/mg TSP) than the CEJ120-12 transgenic line (5 ng/mg TSP) (FIG. 3). Transgenic lines A56-1, -3 and -4 had 3- to 5-fold higher accumulation levels than CEJ120-12, whereas the remaining lines had accumulation levels similar to CEJ120-12 (FIG. 3). Accumulation levels of asialo-rhuEPO in transgenic lines A56-2 and -5 approached approximately 230 ng/mg TSP corresponding to a production level of 0.023% of TSP. The observed expression level of asialo-rhuEPO is considerably higher (more than 50 fold) than the production level of asialoagalacto-rhuEPO in tobacco cells reported by Matsumoto et al. (1995), but similar to asialoagalacto-rhuEPO production levels in tobacco plants reported by Conley et al. (2009).

Quantification of EPO Expression Level in Selected Transgenic Tobacco Lines by qRT-PCR Differences between transgenic tobacco plants transformed with CEJ120 and new genetic cassette A56 are in the promoter and fusion tags. In A56, CaMV 35S$^2$ promoter was used along with DNA sequences encoding a TEV protease cutting site (ENLYFQG), two fusion tags StrepII and KDEL at the C-terminus of the EPO protein. To determine the contribution of CaMV 35S$^2$ promoter toward higher accumulation of asialo-rhuEPO in transgenic plants, qRT-PCR analysis was performed on four high (A56-2, A56-5, A56-11 and A56-12) and two medium (A56-1 and A56-3) asialorhuEPO accumulating lines and compared with CEJ120-12. Results showed that A56-2 and A56-5 lines had much higher transcript levels than other four A56 lines (A56-1, -3, -11 and -12) whereas A56-11 and A56-12 had higher expression levels than lines A56-1 and A56-3 (FIG. 4). These expression data are consistent with protein levels quantified by ELISA in these lines (FIG. 3). When the transcript levels in A56 plants were compared with CEJ120-12, A56-2 and A56-5 had only 1.7-fold and 2.3-fold higher transcript levels. Remaining four A56 transgenic lines had lower expression levels than CEJ120-12 line, which suggest that the contribution of CaMV 35S$^2$ promoter toward high asialo-rhuEPO expression is minor. Considering about 30- to 50-fold higher asialo-rhuEPO accumulation in A56-2, -5, -11 and -12 lines than CEJ120-12 line, the higher protein accumulation should result from an effect of post-transcription. In current study, it could be due to the presence of fusion peptide (StrepII tag) that makes protein more stable and results in high protein accumulation. Such effect has been described previously by Bitonti et al. (2004) and Castilho et al. (2011) who reported that addition of Fc fragment at the C-terminus of EPO leads to enhanced stability and higher accumulation in transgenic plants.

Western Blot Analysis of Asialo-rhuEPO in Selected Transgenic Tobacco Lines

Western blot analysis was performed on soluble leaf extracts of four high (A56-2, A56-5, A56-11 and A56-12) and two medium (A56-1 and A56-3) asialo-rhuEPO expressing lines along with CEJ120-12 in order to verify their sizes and integrity, and further confirm their protein levels observed by ELISA. Equal amount of protein (25 μg) was used for the western blot analysis. As can be seen from FIG. 5, two closely migrating protein bands of size ~28-30 kD were present in the lanes containing the soluble crude protein extracts of A56-1, -3 and CEJ120-12 transgenic tobacco lines when the blot was probed with mouse monoclonal anti-EPO antibody. The presence of two immunoreactive bands was less obvious in high asialo-rhuEPO expressing lines (A56-2, A56-5, A56-11 and A56-12), which may be due to strong signal resulted from higher amount of asialo-rhuEPO in these lines. The intensities of asialo-rhuEPO bands observed in the selected lines are in agreement with the accumulation levels of asialo-rhuEPO as measured by ELISA (see FIG. 3). Both two immunoreactive bands observed on the protein blot correspond to EPOs, but different glycoforms as observed in CEJ120 study (Kittur, et al., 2012). Asialo-rhuEPO produced in tobacco plants was smaller than the rhuEPO expressed in CHO cells (FIG. 5, lane 1). This is because plant-produced asialo-rhuEPO lacks terminal sialic acid residues and tetraantennary N-glycan chains. The enzymes responsible for both of these modifications are absent in plants. The absence of sialic acid and tetraantennary N-glycans in asialo-rhuEPO, however, does not affect its cytoprotective function. In fact, it is an advantage over the commercial EPO made in mammalian cells because plant-produced asialo-rhuEPO lacking its hematopoietic activity prevents thrombosis when high doses of EPO are given in cytoprotective treatments.

Purification of Asialo-rhuEPO from A56-5 Transgenic Tobacco Line

Although a number of EPO purification protocols are reported from mammalian cell cultures, none is available to purify EPO from plant extracts. Matsumoto et al. (1995) described an IAC protocol to purify asialoagalacto-rhuEPO from tobacco cells. However, the antibody used in their purification step is not available commercially and isolating EPO from leaf tissues of tobacco plants is more challenging than from transformed tobacco cells owing to the presence of large quantities of chlorophyll/RuBisCO and secondary metabolites. Conley et al. (2009), despite their higher asialoagalacto-rhuEPO expression levels in their transgenic tobacco plants, failed to obtain pure protein for structural and functional characterization, which may mainly be caused by reasons mentioned above. To exploit the full potential of plant-based expression system for asialo-rhuEPO production for therapeutic purpose, it is important to have a simple purification protocol to obtain reasonably pure protein at low cost. We have developed a simple protocol for the purification of asialo-rhuEPO from transgenic tobacco leaves, involving preliminary fractionation with ammonium sulfate (AS) followed by IAC. We chose A56-5 transgenic tobacco line for protein purification because of its high accumulation of asialo-rhuEPO (230 ng/mg TSP). Solid AS was added to the A56-5 extracts to a final concentration of 25%. We discovered that at this AS concentration most of the chlorophylls are precipitated along with very negligible amount of asialo-rhuEPO. At 65% AS saturation, most of the asialo-rhuEPO was found in the protein pellet. This pellet was then reconstituted in PBS, mixed with ELISA blocking buffer, and applied to the IAC column for further purification as described below.

Since no IAC columns are commercially available, we prepared three IAC columns by immobilizing three different commercially available anti-EPO antibodies and investigated their performance in binding CHO cell-produced rhuEPO exogenously added to crude protein extracts of vector alone transgenic control plant (GUS1) from previous study (Musa et al. 2009). Of the three antibody-coupled columns tested, the rabbit anti-EPO polyclonal antibody column was the most efficient and therefore, this column was used for the purification of asialo-rhuEPO from transgenic tobacco lines. AS precipitated asialo-rhuEPO from A56-5 extract readily bound to the column and could be eluted with 0.1 M glycine-HCl buffer, pH 2.5. Eluted fractions 13-20 (FIG. 6A) were pooled, concentrated and analyzed by western blotting. As can be seen from FIG. 6B, two major immunoreactive bands (lane 2) smaller in size than CHO cell-produced rhuEPO (lane 1) were present on the blot, consistent with the observation of two bands in the crude protein extracts of A56-1 and -3 and CEJ120-12. A minor immunoreactive band was also observed. These three protein bands represent different glycoforms of asialo-rhuEPO.

To further purify immunoaffinity purified asialo-rhuEPO, contaminated BSA from IAC column with many times higher than asialo-rhuEPO was removed as described under "experimental procedures" and subjected to SDS-PAGE analysis. As it is shown in SDS-PAGE profile (FIG. 6C, lane 3), five bands are present in the asialo-rhuEPO fraction obtained from the IAC column with further purification. Based on the position of immunoreactive bands on the western blot (FIG. 6B, lane 2), three protein bands of sizes 31 kD, 28 kD, and 22 kD in SDS-PAGE gel are asialo-rhuEPO, but different glycoforms. Protein band of size ~60 kD corresponds to residual BSA. The identity of the 40 kD protein is not known at this time. Since this two band did not cross-react with anti-EPO antibody, it could be a tobacco protein.

LC-MS/MS Analysis of 30 and 28 kD Two Major Protein Bands

To further confirm whether the two major bands of sizes 28 (band 2) and 30 kD (band 1) (FIG. 6C, lane 3) are really asialo-rhuEPO, they were excised and subjected to protein identification using LC-MS/MS. Six unique peptides, VNFYAWK, SLTTLLR, EAISPPDAASAAPLR, TITADTFR, VYSNFLR and LYTGEACR (representing amino acids 73-79, 131-137, 144-158, 159-166, 171-177 and 182-189 in SEQ ID NO: 4) (FIGS. 7 A-F), covering 31% of the EPO protein sequence (FIG. 8) (Amino acids 28-193 of SEQ ID NO: 4), could be identified from the MS/MS spectra of tryptic peptides of 30 kD protein band. In the case of 28 kD band, seven unique peptides, LICDSR, VNFYAWK, MEVGQQAVEVWQGLALLSEAVLR, EAISPPDAASAAPLR, TITADTFRK, VYSNFLR and LYTGEACR representing amino acids 32-37, 73-79, 81-103, 144-158, 159-167, 171-177 and 182-189 in SEQ ID NO: 4 (FIGS. 9 A-G), covering 45% of the EPO sequence (FIG. 10) (Amino acids 28-193 of SEQ ID NO: 4), could be identified. The above results indicate that both 28 and 30 kD protein bands are EPO, but different glycoforms.

Confirmation of the Presence of β1,4-Linked Galactose Residues on N-Glycan Chains of Purified Asialo-rhuEPO by Binding it to ECA-Agarose Column To investigate whether plant-produced asialo-rhuEPO bears terminal β1,4-linked galactose residues, binding to a β1,4-galactose-specific lectin column (ECA-agarose) was performed. ECA exclusively binds glycan chains containing terminal β1,4-linked galactose residues, which are present only in mammalian glycoproteins (Bakker et al. 2001), but absent in plants (Fitchette-Laine et al. 1997). When immuno-affinity purified asialo-rhuEPO was applied to the ECA-agarose column, it readily bound to the column and could be eluted only with 0.2 M lactose. Asialoagalacto-rhuEPO obtained from plants expressing EPO alone did not bind to it (FIG. 11). These results indicate that asialo-rhuEPO produced in N-glycoengineered transgenic tobacco plants indeed contains β1,4-linked terminal galactose residues. The fact that the N-glycan chains of asialo-rhuEPO bear terminal β1,4-linked galactose residues indicates that GalT is co-expressed in transgenic tobacco plants and is functional.

Binding of Asialo-rhuEPO to EPOR Receptor

Since tissue protective receptor is commercially unavailable, the binding ability of asialo-rhuEPO to hematopoetic receptor EPOR was performed in this invention using an indirect ELISA method developed by Conley et al. (2009). As demonstrated in FIG. 12, asialo-rhuEPO readily interacted with EPOR with saturation reaching around 0.5 nM with a $K_d$ of 0.2 nM, indicating high affinity binding of asialo-rhuEPO to EPOR and thus proper folding of the protein molecule. Asialoagalacto-rhuEPO also showed similar binding curve with a $K_d$ of 0.17 nM. The binding affinities of both asialo- and asialoagalacto-rhuEPO were similar to that of CHO cell-produced rhuEPO ($K_d$=0.12 nM).

Plant-Produced Asialo-rhuEPO Provides a Better Cytoprotective Effect than CHO-Produced rhuEPO To study the cytoprotective function of plant-produced asialo-rhuEPO, its ability to protect neural cells against chemically (staurosporine, STS) induced apoptosis was tested. Neuronal-like N2A neuroblastoma cells were simultaneously treated with 1 μM STS and 20 U/ml plant-produced asialo-rhuEPO or Chinese hamster ovary cells (CHO)-produced rhuEPO (a positive control) for 12 hrs. Cytotoxicity was measured by the amount of lactate dehydrogenase (LDH) released into culture supernatant. Incubation of N2A cells with 1 μM STS alone resulted in 84% cytotoxicity (FIG. 13). In the presence of plant-produced asialo-rhuEPO, however, cytotoxicity was reduced to 47% corresponding to 44% cytoprotection. In the case of CHO-produced rhuEPO, cytotoxicity was reduced to 66% (21% cytoprotection). Based on the above results, plant-produced asialo-rhuEPO has better cytoprotective effect (~2 fold) than CHO-produced rhuEPO.

Plant-Produced Asialo-rhuEPO Cytoprotection Against STS-Induced Neural Cell Damage is Via JAK2 Activation JAK2 activation (phosphorylation) following EPO stimulation has been demonstrated in both neural (Digicaylioglu et al. 2001) and non-neural tissues (Yokomaku, et al. 2008), and is thought to be responsible for cytoprotective effect of EPO. To verify the plant-produced asialo-rhuEPO-induced signaling in N2A cells, phosphorylation of JAK2 in response to plant-produced asialo-rhuEPO or CHO-produced EPO treatment was investigated. Western blot analysis was performed on cell lysates that were prepared from untreated, STS-treated, CHO-produced rhuEPO+STS, and plant produced asialo-rhuEPO+STS treated cells for 3 and 6 hrs. Western blot of cell lysates from both 3- and 6-hr treatments showed a phosphorylated JAK2 (p-JAK2) band with slightly higher intensity in CHO-produced rhuEPO+STS and plant produced asialo-rhuEPO+STS treated cells than untreated and STS alone treated cells (FIG. 14). When blot was stripped and re-probed with anti-JAK2 antibody, the intensity of total JAK2 band was found to be similar in untreated, STS-treated and two types of EPO-treated samples, indicating that JAK2 is activated by both plant-produced asialo-rhuEPO and CHO-produced rhuEPO. These results imply that plant-produced rhuEPO mediates its cytoprotective effect via activation of JAK2.

Caspase 3 is an executioner caspase of apoptotic pathway (Jacobson et al. 1996). It can be expected that caspase 3 will be induced during apoptosis process. To test whether induced expression of caspase 3 can be affected by EPO treatment, we performed western blot analysis on cell lysates that were prepared from untreated, STS alone, CHO-produced rhuEPO+STS, and plant produced asialo-rhuEPO+STS treated cells for 3 and 6 hrs. When cell lysates from 3-hr treated cells were analyzed, no caspase 3 band was observed in either sample. When cells were treated for 6 hrs, active caspase 3 fragments (19 kD) were clearly visible in cell lysates prepared from STS and CHO-produced rhuEPO+STS treated cells (FIG. 14). However, the band intensity in CHO-produced rhuEPO+STS treated cell lysate was much lesser than that in STS-treated cell lysate. Although we also observed a 19 kD active caspase 3 band in plant-produced asialo-rhuEPO treated cell lysate, it is very faint compared to STS-treated cell lysate. The appearance of active caspase 3 band intensities in these samples is consistent their cytotoxicities observed, which are 84%, 66% and 47% in STS alone, CHO-produced rhuEPO+STS and plant-produced asialo-rhuEPO+STS treated cells, respectively.

REFERENCES

Bakker H, Bardor M, Molthoff J W, Gomord V, Elbers I, Stevens L H, Jordi W, Lommen A, Faye L, Lerouge P, Bosch D. 2001. Galactose-extended glycans of antibodies produced by transgenic plants. *Proc Nat Acad Sci USA.* 98:2899-2904.

Bakker H, Rouwendal G J, Karnoup A S, Florack D E, Stoopen G M, Helsper J P, van Ree R, van Die I, Bosch D. 2006. An antibody produced in tobacco expressing a hybrid beta-1,4-galactosyltransferase is essentially devoid of plant carbohydrate epitopes. *Proc Nat Acad Sci USA.* 103:7577-7582.

Bitonti A J, Dumont J A, Low S C, Peters R T, Kropp K E, Palombella V J, Stattel J M, Lu Y, Tan C A, Song J J, Garcia A M, Simister N E, Spiekermann G M, Lencer W I, Blumberg R S. 2004. Pulmonary delivery of an erythropoietin Fc fusion protein in non-human primates through an immunoglobulin transport pathway. *Proc Natl Acad Sci USA,* 101:9763-9768.

Brines M L, Ghezzi P, Keenan S, Agnello D, de Lanerolle N C, Cerami C, Itri L M, Cerami A. 2000. Erythropoietin crosses the blood-brain barrier to protect against experimental brain injury. *Proc Natl Acad Sci USA.* 97:10526-10531.

Brines M, Cerami A, Cerami C. Protection, restoration, and enhancement of erythropoietin-responsive cells, tissues and organs. Patent WO2002/053580.

Brines M, Grasso G, Fiordaliso F, Sfacteria A, Ghezzi P, Fratelli M, Latini R, Xie Q W, Smart J, Su-Rick C J, Pobre E, Diaz D, Gomez D, Hand C, Coleman T, Cerami A. 2004. Erythropoietin mediates tissue protection through an erythropoietin and common beta-subunit heteroreceptor. *Proc Natl Acad Sci USA.* 101:14907-14912.

Brines M, Patel N S A, Villa P, Brines C, Mennini T, De Paola M, Erbayraktar Z, Erbayraktar S, Sepodes S, Thiemermann C, Ghezzi P, Yamin M, Hand C C, Xie Q, Coleman T, Cerami A. 2008. Nonerythropoietic, tissue-protective peptides derived from the tertiary structure of erythropoietin. *Proc Natl Acd Sci USA.*105:10925-10930.

Calvillo L, Latini R, Kajstura J, Leri A, Anversa P, Ghezzi P, Salio M, Cerami A, Brines M. 2003. Recombinant human erythropoietin protects the myocardium from ischemia-reperfusion injury and promotes beneficial remodeling. *Proc Natl Acad Sci USA.* 100:4802-4806.

Castilho A, Gattinger P, Grass J, Jez1 J, Pabst M, Altmann F, Gorfer M, Strasser R, Steinkellner H. 2011. N-glycosylation engineering of plants for the biosynthesis of glycoproteins with bisected and branched complex N-glycans. *Glycobiology.* 21:813-823.

Cheon B Y, Kim H J, Oh K H, Bahn S C, Ahn J H, Choi J W, Ok S H, Bae J M, Shin J S. 2004. Overexpression of human erythropoietin (EPO) affects plant morphologies: retarded vegetative growth in tobacco and male sterility in tobacco and *Arabidopsis. Transgenic Res.* 13:541-549.

Conley A J, Mohib K, Jevnikar A M, Brandle J E. 2009. Plant recombinant erythropoietin attenuates inflammatory kidney cell injury. *Plant Biotechnol J.* 7:183-199.

Conrad U, Fiedler U. 1998. Compartment-specific accumulation of recombinant immunoglobulins in plant cells: an essential tool for antibody production and immunomodulation of physiological functions and pathogen activity. *Plant Mol Biol.* 38:101-109.

Digicaylioglu M, Lipton S A. 2001. Erythropoietin-mediated neuroprotection involves cross-talk between Jak2 and NF-κB signaling cascades. *Nature* 412(6847):641-647.

Yokomaku Y, et al. 2008. Asialoerythropoietin prevents contrast-induced nephropathy. *J Am Soc Nephrol* 19(2): 321-328. Denecke J, Botterman J, Deblaere R. 1990. Protein secretion in plant cells can occur via a default pathway. *Plant Cell.* 2:51-59.

Edmund G T, Wee D, Sherrier J, Prime T A, Dupree P. 1998. Targeting of Active Sialyltransferase to the Plant Golgi Apparatus. *Plant Cell.* 10:1759-1768.

Elliott S, Giffin J, Suggs S, Lau E P, Banks A R. 1989. Secretion of glycosylated human erythropoietin from yeast directed by the alpha-factor leader region. *Gene.* 79:167-180.

Erbayraktar S, Grasso G, Sfacteria A, Xie Q W, Coleman T, Kreilgaard M, Torup L, Sager T, Erbayraktar Z, Gokmen N, Yilmaz O, Ghezzi P, Villa P, Fratelli M, Casagrande S, Leist M, Helboe L, Gerwein J, Christensen S, Geist M A, Pedersen L O, Cerami-Hand C, Wuerth J P, Cerami A, Brines M. 2003. Asialoerythropoietin is a nonerythropoietic cytokine with broad neuroprotective activity in vivo. *Proc Natl Acad Sci USA.* 100:6741-6746.

Fiordaliso F, Chimenti S, Staszewsky L, Bai A, Carlo E, Cuccovillo I, Doni M, Mengozzi M, Tonelli R, Ghezzi P, Coleman T, Brines M, Cerami A, Latini R. 2005. A nonerythropoietic derivative of erythropoietin protects the myocardium from ischemia-reperfusion injury. *Proc Natl Acad Sci USA.* 102:2046-2051.

Fitchette-Laine A, Gomard V, Cabones M, Michalski J, Saint Macary M, Foucher B, *Cavalier B, Hawes C, Lerouge P, Faye L.* 1997. N-glycan harboring the lewis a epitope are expressed at the surface of plant cells. *Plant J.* 12:1411-1417.

Fisher J W. 2003. Erythropoietin: physiology and pharmacology update. *Exp Biol Med* (Maywood). 288:1-14.

Fukuda M N, Sasaki H, Lopez L, Fukuda M. 1989. Survival of recombinant erythropoietin in the circulation: the role of carbohydrates. *Blood.* 73:84-89.

Genc S, Koroglu T F, Genc K. 2004. Erythropoietin as a novel neuroprotectant. *Restor Neurol Neurosci.* 22:105-119.

Gomord V, Faye L. 2004. Posttranslational modification of therapeutic proteins in plants. *Curr Opin Plant Biol.* 7:171-181.

Gong H, Wang W, Kwon T H, Jonassen T, Li C, Ring T, FrøkiAEr J, Nielsen S. 2004. EPO and alpha-MSH prevent ischemia/reperfusion-induced down-regulation of AQPs and sodium transporters in rat kidney. *Kidney Int.* 66:683-695.

Higuchi M (Shizuoka, J P) Method for removing sialic acid and method for producing asialoerythropoietin. Patent application number: 20090005540.

Holsters M, de Waele D, Depicker A, Messens E, Van Montagu M, Schell J. 1978. Transfection and transformation of *Agrobacterium tumefaciens. Mol Gen Genet.* 163:181-187.

Hung C Y, Sun Y H, Chen J J, Darlington D E, Williams A L, Burkey K O, Xie J H. 2010. Identification of a Mg-protoporphyrin IX monomethyl ester cyclase homologue, EaZIP, involved in variegation of *Epipremnum aureum* 'Golden Pothos' is achieved through a unique method of comparative study using tissue regenerated plants. *J Exp Bot.* 61:1483-1493.

Jacobs K, Shoemaker C, Rudersdorf R, Neill S D, Kaufman R J, Mufson A, Seehra J, Jones S S, Hewick R, Fritsch E F, Kawakita M, Shimizu T, Miyake T. 1985. Isolation and characterization of genomic and cDNA clones of human erythropoietin. *Nature.* 313:806-810.

Jacobson M D, Weil M, Raff M C. 1996. Role of Ced-3/ICE-family proteases in staurosporine-induced programmed cell death. *J Cell Biol* 133(5):1041-1051.

Jelkmann W. 2005. Effects of erythropoietin on brain function. *Curr Pharm Biotechnol.* 6:65-79.

Jelkmann W. 1992. Erythropoietin: structure, control of production, and function. *Physiol Rev.* 72:449-489.

Kim Y K, Shin H S, Tomiya N, Lee Y C, Betenbaugh M J, Cha H J. 2005. Production and N-glycan analysis of secreted human erythropoietin glycoprotein in stably transfected *Drosophila* S2 cells. *Biotechnol Bioeng.* 92:452-461.

Kittur F S, Hung C-Y, Darlington D E, Sane D C, Xie J H. 2012. N-Glycoengineering of tobacco plants to produce cytoprotective asialoerythropoietin. Plant Cell Rep. DOI 10.1007/s00299-012-1244-x.

Krantz S B, Jacobson L O. 1970. Erythropoietin and the regulation of erythropoiesis (University of Chicago Press, Chicago, 1970).

Krantz S B. 1991. Erythropoietin. *Blood.* 77:419-434.

Lee-Huang S. 1984. Cloning and expression of human erythropoietin cDNA in *Escherichia coli. Proc Natl Acad Sci USA.* 81:2708-2712.

Leist M, Ghezzi P, Grasso G, Bianchi R, Villa P, Fratelli M, Savino C, Bianchi M, Nielsen J, Gerwien J, Kallunki P, Larsen A K, Helboe L, Christensen S, Pedersen L O, Nielsen M, Torup L, Sager T, Sfacteria A, Erbayraktar S, Erbayraktar Z, Gokmen N, Yilmaz O, Cerami-Hand C, Xie Q W, Coleman T, Cerami A, Brines M. 2004. Derivatives of erythropoietin that are tissue protective but not erythropoietic. *Science.* 305:239-242.

Lerouge P, Cabanes-Macheteau M, Rayon C, Fischette-Laine A C, Gomord V, Faye L. 1998. N-glycoprotein biosynthesis in plants: recent developments and future trends. *Plant Mol Biol.* 38:31-48.

Ma J K, Drake P M, Christou P. 2003. The production of recombinant pharmaceutical proteins in plants. *Nat Rev Genet.* 4:794-805.

Maiti I B, Murphy J F, Shaw J G, Hunt A G. 1993. Plants that express a potyvirus proteinase gene are resistant to virus infection. *Proc Natl Acad Sci USA.* 90:6110-6114.

Matsumoto S, Ikura K, Ueda M, Sasaki R. 1995. Characterization of a human glycoprotein (erythropoietin) produced in cultured tobacco cells. *Plant Mol Biol.* 27:1163-1172.

Misaki R, Kimura Y, Palacpac N Q, Yoshida S, Fujiyama K, Seki T. 2003. Plant cultured cells expressing human β1,4-galactosyltransferase secrete glycoproteins with galactose-extended N-linked glycans. *Glycobiology.* 13:199-205.

Moon C, Krawczyk M, Ahn D, Ahmet I, Paik D, Lakatta E G, Talan M I. 2003. Erythropoietin reduces myocardial infarction and left ventricular functional decline after coronary artery ligation in rats. *Proc Natl Acad Sci USA.* 100:11612-11617.

Morell A G, Gregoriadis G, Scheinberg I H, Hickman J, Ashwell G. 1971. The role of sialic acid in determining the survival of glycoproteins in the circulation. *J Biol Chem.* 246:1461-1467.

Morishita E, Masuda S, Nagano M, Yasuda Y, Sasaki R. 1997. Erythropoietin receptor is expressed in rat hippocampal and cerebral cortical neurons, and erythropoietin prevents in vitro glutamate-induced neuronal death. *Neuroscience.* 76:105-116.

Musa T A, Hung C Y, Darlington D E, Sane D C, Xie J H. 2009. Overexpression of human erythropoietin in tobacco does not affect plant fertility or morphology. *Plant Biotechnol Rep.* 3:157-165.

Palacpac N Q, Yoshida S, Sakai H, Kimura Y, Fujiyama K, Yoshida T, Seki T. 1999. Stable expression of human beta1,4-galactosyltransferase in plant cells modifies N-linked glycosylation patterns. *Proc Natl Acad Sci USA.* 96:4692-4697.

Parsa C J, Kim J, Riel R U, Pascal L S, Thompson R B, Petrofski J A, Matsumoto A, Stamler J S, Koch W J. 2004. Cardioprotective effects of erythropoietin in the reperfused ischemic heart: a potential role for cardiac fibroblasts. *J Biol Chem.* 279:20655-20662.

Quelle F W, Caslake L F, Burkert R E, Wojchowski D M. 1989. High-level expression and purification of a recombinant human erythropoietin produced using a baculovirus vector. *Blood.* 74:652-657.

Robic G, Lacorte C, Rech E L, Miranda E A. 2011. Application of electrochemically produced aluminum hydroxide gel for prepurification of recombinant synthetic green fluorescent protein produced in tobacco leaves. *Biotechnol Prog.* 27:1029-1035.

Sasaki H, Bothner B, Dell A, Fukuda M. 1987. Carbohydrate structure of erythropoietin expressed in Chinese hamster ovary cells by a human erythropoietin cDNA. *J Biol Chem.* 262:12059-12076.

Smith K J, Bleyer A J, Little W C, Sane D C. 2003. The cardiovascular effects of erythropoietin. *Cardiovasc Res.* 59:538-548.

Sherwood J B. 1984. The chemistry and physiology of erythropoietin. *Vitam Horm.* 41:161-211.

Staudacher E, Dalik, T, Wawra, P, Altmann F, Marz L.1995. Functional purification and characterization of a GDP-fucose:β-N-acetylglucosamine (Fuc to Asn linked GlcNac) α1,3-fucosyltransferase from mung beans. *Glycoconjugate J.* 12:780-786.

Takeuchi M, Kobata A. 1991. Structures and functional roles of the sugar chains of human erythropoietins. *Glycobiology.* 1:337-346.

Toledo J R, Sanchez O, Segui R M, Garcia G, Montanez M, Zamora P A, Rodriguez M P, Cremata J A. 2006. High expression level of recombinant human erythropoietin in the milk of non-transgenic goats. *J Biotechnol.* 123:225-235.

Tucker J, Yakatan S. 2008. *Biogenerics* 2007: how far have we come? *J Comm Biotechnol.* 14:56-64.

Wang X, Zhu C, Wang X, Gerwien J G, Schrattenholz A, Sandberg M, Leist M, Blomgren K. 2004. The noneryth-ropoietic asialoerythropoietin protects against neonatal hypoxia-ischemia as potently as erythropoietin. *J Neurochem.* 91:900-910.

Wasley L C, Timony G, Murtha P, Stoudemire J, Dorner A J, Caro J. 1991. The importance of N- and O-linked oligosaccharides for the biosynthesis and in vitro and in vivo biologic activities of erythropoietin. *Blood.* 77:2624-2632

Wee E G, Sherrier D J, Prime T A, Dupree P. 1998. Targeting of active sialyltransferase to the plant Golgi apparatus. *Plant Cell.* 10:1759-1768.

Weise A, Altmann F, Rodriguez-Franco M, Sjoberg E R, Baumer W, Launhardt H, Kietzmann M, Gorr G. 2007. High-level expression of secreted complex glycosylate recombinant human erythropoietin in the *Physcomitrella* Δ-fuc-t Δ-xyl-t mutant. *Plant Biotech J.* 5:389-401.

Wiessner C, Allegrini P R, Ekatodramis D, Jewell U R, Stallmach T, Gassmann M. 2001. Increased cerebral infarct volumes in polyglobulic mice overexpressing erythropoietin. *J Cereb Blood Flow Metab.* 21:857-864.

Yokomaku Y, et al. 2008. Asialoerythropoietin prevents contrast-induced nephropathy. *J Am Soc Nephrol* 19(2): 321-328.

Zeng Y, Bannon G, Thomas V H, Rice K, Drake R, Elbein A. 1997. Purification and specificity of β1,4-xylosytransferase, an enzyme that contributes to the allergenicity of some plant proteins. *J Biol Chem.* 272:31340-31347.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. This application claims the benefit of U.S. Provisional Patent Application No. 61/652,599, filed May 29, 2012, which is hereby incorporated herein in its entirety by reference.

Although the invention has been described herein in some detail by way of illustration and example for purposes of clarity of understanding, it will be obvious that certain changes and modifications may be practiced within the scope of the appended embodiments.

That which is claimed:

1. A method for the high-level production and purification of asialoerythropoietin (asialo-rhuEPO) in a plant or plant cell comprising:

(a) obtaining a transformed tobacco plant or transformed tobacco plant cell, wherein the transformed plant or transformed plant cell comprises a first promoter that drives expression in a plant cell operably linked to a first polynucleotide encoding a human erythropoietin (EPO) fusion protein and a second promoter that drives expression in a plant cell operably linked to a second polynucleotide encoding a $\beta$1,4-galactosyltransferase; wherein the human EPO fusion protein is encoded by a nucleic acid sequence selected from the group consisting of:

(1) the nucleic acid sequence set forth in SEQ ID NO: 3; and (2) a nucleic acid sequence encoding the amino acid sequence set forth in SEQ ID NO: 4; and wherein the second polynucleotide comprises a nucleic acid sequence selected from the group consisting of:

(1) the nucleic acid sequence set forth in SEQ ID NO: 10; and (2) a nucleic acid sequence encoding the amino acid sequence set forth in SEQ ID NO: 11;

(b) making an aqueous extract of plant tissue, wherein the plant tissue comprises asialo-rhuEPO;

(c) removing chlorophyll and/or RuBisCO protein from the aqueous extract via ammonium sulfate precipitation;

(d) binding the asialo-rhuEPO in the aqueous extract to an immune affinity column, wherein the immune affinity column is a rabbit anti-EPO polyclonal antibody column; and (e) eluting the bound asialo-rhuEPO from the immune affinity column;

wherein at least 100 ng of asialo-rhuEPO per mg of total soluble protein is recovered; and wherein the asialo-rhuEPO comprises terminal $\beta$1,4-galactose residues.

2. The method of claim 1, wherein the human EPO fusion protein comprises a human EPO domain and optionally further comprises at least one operably linked additional domain selected from the group consisting of a protease cleavage domain, a tag domain, and an endoplasmic reticulum (ER) retention signal domain.

3. The method of claim 1, wherein the $\beta$1,4-galactosyltransferase is a mammalian $\beta$1,4-galactosyltransferase.

4. The method of claim 1, wherein the $\beta$1,4-galactosyltransferase is a human $\beta$1,4-galactosyltransferase.

5. The method of claim 1, further comprising making the transformed plant or transformed plant cell, wherein the transformed plant or transformed plant cell comprises a first nucleic acid construct comprising the first promoter operably linked to the first polynucleotide and a second nucleic acid construct comprising the second promoter operably linked to the second polynucleotide.

6. The method of claim 5, further comprising regenerating the transformed plant cell into a transformed plant.

7. The method of claim 1, further comprising growing the transformed plant or transformed plant cell under conditions favorable for the production of asialo-rhuEPO, whereby the transformed plant, plant part, plant cell, or seed thereof or the transformed plant cell produces a high level of asialo-rhuEPO.

8. The method of claim 1, further comprising purifying the asialo-rhuEPO from the transformed plant, the transformed plant cell, or a part, cell, or seed of the transformed plant.

9. The method of claim 1, wherein the transformed plant or part thereof, or the transformed plant cell, produces a high level of asialo-rhuEPO when grown under conditions favorable for the production of asialo-rhuEPO.

10. The method of claim 1, wherein the human EPO fusion protein comprises, in operable linkage and in the following order from N-terminal to C-terminal end, a human EPO domain, a protease cleavage domain, a tag domain, and an endoplasmic reticulum (ER) retention signal domain.

11. The method of claim 1, wherein at least 200 ng of asialo-rhuEPO per mg of total soluble protein is recovered.

12. The method of claim 1, wherein at least 250 ng of asialo-rhuEPO per mg of total soluble protein is recovered.

\* \* \* \* \*